(12) United States Patent
Craig et al.

(10) Patent No.: US 11,103,425 B2
(45) Date of Patent: Aug. 31, 2021

(54) INORGANIC DENTAL FILLERS INCLUDING A SILANE TREATED SURFACE

(71) Applicant: 3M INNOVATIVE PROPERTIES COMPANY, St. Paul, MN (US)

(72) Inventors: Bradley D. Craig, Lake Elmo, MN (US); Paul J. Homnick, Lake Elmo, MN (US); Ahmed S. Abuelyaman, Woodbury, MN (US); Thomas P. Klun, Lakeland, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/954,742

(22) PCT Filed: Dec. 18, 2018

(86) PCT No.: PCT/IB2018/060272
§ 371 (c)(1),
(2) Date: Jun. 17, 2020

(87) PCT Pub. No.: WO2019/123263
PCT Pub. Date: Jun. 27, 2019

(65) Prior Publication Data
US 2020/0315924 A1 Oct. 8, 2020

Related U.S. Application Data

(60) Provisional application No. 62/608,699, filed on Dec. 21, 2017.

(51) Int. Cl.
*A61K 6/853* (2020.01)
*A61K 6/20* (2020.01)
*A61K 6/887* (2020.01)

(52) U.S. Cl.
CPC ............... *A61K 6/853* (2020.01); *A61K 6/20* (2020.01); *A61K 6/887* (2020.01)

(58) Field of Classification Search
CPC .................................................. A61K 6/887
See application file for complete search history.

(56) References Cited

U.S. PATENT DOCUMENTS

| | | | |
|---|---|---|---|
| 4,642,126 | A | 2/1987 | Zador |
| 4,650,889 | A | 3/1987 | Plueddemann |
| 4,652,274 | A | 3/1987 | Boettcher |
| 5,154,762 | A | 10/1992 | Mitra |
| 5,192,815 | A | 3/1993 | Okada |
| 5,501,727 | A | 3/1996 | Wang |
| 5,545,676 | A | 8/1996 | Palazzotto |
| 5,696,179 | A | 12/1997 | Chawla |
| 5,888,491 | A | 3/1999 | Mitra |
| 5,918,772 | A | 7/1999 | Keller |
| 5,944,419 | A | 8/1999 | Streiff |
| 6,572,693 | B1 | 6/2003 | Wu |
| 6,730,156 | B1 | 5/2004 | Windisch |
| 6,982,288 | B2 | 1/2006 | Mitra |
| 7,173,074 | B2 | 2/2007 | Mitra |
| 7,674,850 | B2 | 3/2010 | Karim |
| 7,816,423 | B2 | 10/2010 | Karim |
| 8,314,264 | B2 | 11/2012 | Tsuchida |
| 8,367,748 | B2 | 2/2013 | Moszner |
| 8,647,510 | B2 | 2/2014 | Kolb |
| 8,710,113 | B2 | 4/2014 | Eckert |
| 8,822,564 | B2 | 9/2014 | Drechsler |
| 8,900,556 | B2 | 12/2014 | Oxman |
| 8,906,981 | B2 | 12/2014 | Yang |
| 9,050,252 | B2 | 6/2015 | Craig |
| 9,056,043 | B2 | 6/2015 | Joly |
| 9,403,966 | B2 | 8/2016 | Joly |
| 9,790,396 | B2 | 10/2017 | Klun |
| 9,982,160 | B2 | 5/2018 | Klun |
| 10,011,735 | B2 | 7/2018 | Klun et al. |
| 10,533,111 | B2 | 1/2020 | Klun et al. |
| 2004/0122126 | A1 | 6/2004 | Wu |

(Continued)

FOREIGN PATENT DOCUMENTS

| | | |
|---|---|---|
| EP | 0732911 | 9/1996 |
| JP | 03-070778 | 3/1991 |

(Continued)

OTHER PUBLICATIONS

Buruiana, "Photopolymerization Experiments and Properties of Some Urethane/Urea Methacrylates Tested in Dental Composites", Journal of Composite Materials, 2012, vol. 46, No. 4, pp. 371-382.

Database EPODOC [Online] European Patent Office, The Hague, NL, Nov. 9, 2015, "Novel Silane Coupling Agent and Dental Composition Comprising the Same", XP002793934, Database accession No. JP20140087703 abstract & JP 2015 196682 A (Shofu Inc; Mitsui Chemicals Inc), 4 pages.

Database WPI Week 201579, Nov. 9, 2015 Thomson Scientific, London, GB, AN 2015-68957Q XP002790952, & JP 2015 196684 A (Matsukaze KK) abstract 2 pages.

Fuchigmi, "Precision Synthesis of a Long-Chain Silane Coupling Agent Using Micro Flow Reactors and Its Application in Dentistry", Journal of Encapsulation and Adsorption Sciences, Jan. 2016, vol. 06, No. 01, pp. 35-46.

(Continued)

*Primary Examiner* — Michael F Pepitone
(74) *Attorney, Agent, or Firm* — 3M IPC

(57) ABSTRACT

The present disclosure provides an inorganic dental filler including a surface treated with at least one silane. Exemplary silanes described in the present disclosure for the surface treatment of the inorganic filler include silanes of Formula I and/or Formula II: $(R^{Si})$—$(CR^1R^2)_n$—(NH—C(O)—O—$CH_2$—$CH_2)_q$—$N(R^5)$—C(O)—NH—($CH_2$—$CH_2$—O)$_r$—$CR^3R^4$—$CH_2$-(A) Formula I $(R^{Si})$—$(CR^1R^2)_n$—NH—C(O)—O—$CR^3R^4$-(L)$_q$-$CH_2$-(A) Formula II, wherein: $R^{Si}$ is a silane-containing group of the formula —$Si(Y_p)(R^6)_{3-p}$, wherein Y is a hydrolysable group, $R^6$ is a monovalent alkyl or aryl group, and p is 1, 2, or 3. Methods of making and using the surface treated inorganic dental fillers are also disclosed.

20 Claims, No Drawings

(56) References Cited

U.S. PATENT DOCUMENTS

| | | |
|---|---|---|
| 2006/0187752 A1 | 8/2006 | Keller |
| 2006/0247329 A1 | 11/2006 | Moszner |
| 2007/0090079 A1 | 4/2007 | Keller |
| 2010/0210862 A1 | 8/2010 | Tsuchida |
| 2015/0203707 A1 | 7/2015 | Klun |
| 2015/0218294 A1 | 8/2015 | Klun |
| 2020/0069535 A1 | 3/2020 | Agre et al. |

FOREIGN PATENT DOCUMENTS

| | | |
|---|---|---|
| JP | 04-018453 | 1/1992 |
| JP | 2015-196682 | 11/2015 |
| JP | 2015-196683 | 11/2015 |
| JP | 2015-196684 | 11/2015 |
| JP | 2015-196687 | 11/2015 |
| JP | 2016-194027 | 11/2016 |
| JP | 6039349 | 11/2016 |
| JP | 6072493 | 1/2017 |
| WO | WO 1995-015740 | 6/1995 |
| WO | WO 2001-008639 | 2/2001 |
| WO | WO 2001-030307 | 5/2001 |
| WO | 2005-016783 | 2/2005 |
| WO | 2007-104037 | 9/2007 |
| WO | 2009-061884 | 5/2009 |
| WO | 2010-123800 | 10/2010 |
| WO | 2011-149631 | 12/2011 |
| WO | 2014-025384 | 2/2014 |
| WO | 2014-025385 | 2/2014 |
| WO | 2014-025386 | 2/2014 |
| WO | 2016-126103 | 8/2016 |
| WO | 2017-015193 | 1/2017 |
| WO | 2018-213074 | 11/2018 |

OTHER PUBLICATIONS

Karabela, "Synthesis and Study of Physical Properties of Dental Light-Cured Nanocomposites using Different Amounts of a Urethane Dimethacrylate Trialkoxysilane Coupling Agent", Dental Materials, Aug. 2011, vol. 27, No. 11, pp. 1144-1152.

Sakaguchi, Craig'S Restorative Dental Materials, Thirteenth Edition., Elsevier, 86 (2012).

International Search Report for PCT International Application No. PCT/IB2018/060272, dated Sep. 30, 2019, 7 pages.

INORGANIC DENTAL FILLERS INCLUDING A SILANE TREATED SURFACE

CROSS REFERENCE TO RELATED APPLICATIONS

This application is a national stage filing under 35 U.S.C. 371 of PCT/IB2018/060272, filed 18 Dec. 2018, which claims the benefit of U.S. Provisional Application No. 62/608,699, filed 21 Dec. 2017, the disclosures of each of which are incorporated by reference herein in their entireties.

BACKGROUND

Shrinkage and shrinkage stress are a continual problem in numerous applications involving free radically cured thermoset materials, and more specifically, dental composite materials. Dental composite materials are typically made from a combination of a free radically cured resin material (e.g., a (meth)acrylate resin), an initiator package, and silane treated inorganic filler particles. When these thermoset materials polymerize, they shrink, which can induce stresses to the surrounding tooth structure to which they are bonded, causing problems such as microleakage (leading to secondary decay), debonding of the adhesive, fracture of the tooth, or post-operative sensitivity (e.g., pain for the patient). This issue has further been exacerbated by the trend for composite materials in the mouth to be cured to deeper and deeper increments, leading to higher stresses from "bulk" placement. As materials are cured in larger increments, the need for stress reduction increases, since the ability to reduce the stresses though the traditional "C-factor" control through layering is reduced.

Reported attempts to reduce the stresses encountered when curing hardenable dental compositions by changing resin composition with respect to molecular weight, mobility limitations of the radicals, and chain transfer mechanisms have met with limited success.

There is a continuing need for new materials and methods that can reduce the stresses encountered when curing hardenable dental compositions.

SUMMARY

Surface modified inorganic filler particles often serve as natural stress concentrators, typically having multiple reactive groups attached to a rigid inorganic particle. A silane often used to surface modify inorganic particles is 3-methacryloxypropyltrimethoxysilane. Reported attempts to incorporate alternative (meth)acrylate functional silanes have not resulted in significant stress reduction, and often have led to an increase in the stress profile of materials treated with alternative silanes. Stress can be reduced by replacing the methacrylate functional silane with non-functional silanes, but at the expense of mechanical properties.

Disclosed herein are dental fillers that include an inorganic dental filler having a surface treated with at least one (meth)acrylated silane, which can include urethane and/or urea groups in the organic portion of the silane. Dental compositions that include these disclosed inorganic dental fillers having a surface treated with at least one (meth)acrylated silane can exhibit reduced stresses encountered when curing the hardenable dental compositions. In some embodiments, the hardened dental compositions disclosed herein can allow for significant stress reduction (e.g., 25-50% stress reduction) while maintaining satisfactory mechanical properties of the final composite. In some embodiments, the dental fillers disclosed herein can have improved compatibility with low-stress urethane methacrylate monomers available in the market.

In one aspect, the present disclosure provides an inorganic dental filler including a surface treated with at least one silane.

In one embodiment, the at least one silane is of the formula:

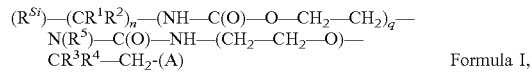

Formula I, wherein: $R^{Si}$ is a silane-containing group of the formula $-Si(Y_p)(R^6)_{3-p}$, wherein Y is a hydrolysable group, $R^6$ is a monovalent alkyl or aryl group, and p is 1, 2, or 3; each $R^1$, $R^2$, and $R^3$ is independently H, an alkyl group, an aryl group, an alkaryl group, or an aralkyl group; $R^4$ is H, an alkyl group, an aryl group, an alkaryl group, an aralkyl group, or a group of the formula $-(CH_2)_m-(A)$, wherein m is 1 to 6; n is 1 to 6; q is 0 or 1; t is 0 or 1; A is a (meth)acryl group of the formula $X^1-C(O)-C(R^7)=CH_2$, wherein $X^1$ is $-O$, $-S$, or $-NR^7$, and each $R^7$ is independently H or a $C_1-C_4$ alkyl group; and $R^5$ is H, an alkyl group, a cycloalkyl group, an aryl group, an alkaryl group, an aralkyl group, a group of the formula $(R^{Si})-(CR^1R^2)-(NH)-C(O)-O-CH_2-CH_2)_q-$, a group of the formula $(R^{Si})-(CR^1R^2)_n-NH-C(O)-N(R')-(CH_2)_m-$, a group of the formula $-(CH_2)_m-(A)$, a group of the formula $-(CH_2)_n-N(R')-C(O)-NH-(CH_2-CH_2-O)_t-CR^3R^4-CH_2-(A)$, or a group of the formula $-(CH_2)_m-N(R^{Si})-C(O)-NH-R^9$; wherein each m and n is independently 1 to 6, q is 0 or 1, t is 0 or 1, and each $R^1$, $R^2$, $R^3$, $R^4$, $R^{Si}$, and A are as defined above; $R^8$ is H or a group of the formula $-(CH_2)_m-NH-C(O)-NH-(CH_2-CH_2-O)_t-CR^3R^4-CH_2-(A)$, a group of the formula $-(CH_2)_m-NH-C(O)-NH-(CR^1R^2)-(R^{Si})$, or a group of the formula $-(CH_2)_m-NH-C(O)-NH-R^9$, wherein each m and n is independently 1 to 6, t is 0 or 1, and each $R^1$, $R^2$, $R^3$ $R^4$, $R^{Si}$, and A are as defined above; and $R^9$ is an alkyl group, an aryl group, an alkaryl group, or an aralkyl group; with the proviso that at least one of $R^1$, $R^2$, $R^3$, $R^4$, and $R^5$ is not H.

In another embodiment, the at least one silane is of the formula:

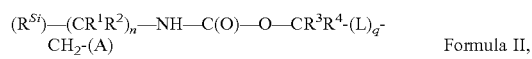

Formula II, wherein: $R^{Si}$ is a silane-containing group of the formula $-Si(Y_p)(R^6)_{3-p}$, wherein Y is a hydrolysable group, $R^6$ is a monovalent alkyl or aryl group, and p is 1, 2, or 3; each $R^1$, $R^2$, and $R^3$ is independently H, an alkyl group, an aryl group, an alkaryl group, or an aralkyl group; $R^4$ is H, an alkyl group, an aryl group, an alkaryl group, or an aralkyl group, wherein the group may optionally be substituted with one or more catenary oxygen atoms, $-O-C(O)-$ groups, and/or $-C(O)-O-$ groups; n is 1 to 6; q is 0 or 1; L is a divalent alkylene group, a divalent arylene group, a divalent alkarlyene group, or a divalent aralkylene group, wherein the divalent group may optionally be substituted with one or more catenary oxygen atoms, $-O-C(O)-$ groups, and/or $-C(O)-O-$ groups; and A is a (meth)acryl group of the formula $X^1-C(O)-C(R^7)=CH_2$, wherein $X^1$ is $-O$, $-S$, or $-NR^7$, and each $R^7$ is independently H or a $C_1-C_4$ alkyl group; with the proviso that at least one of $R^1$, $R^2$, $R^3$, and $R^4$ is not H.

In another aspect, the present disclosure provides a hardenable dental composition that includes a surface treated inorganic dental filler as disclosed herein.

In another aspect, the present disclosure provides a method of preparing a surface treated inorganic dental filler as disclosed herein, the method including contacting an inorganic filler with at least one silane of Formula I or Formula II as described herein.

In another aspect, the present disclosure provides a hardened dental composition including a surface treated inorganic dental filler as described herein.

In another aspect, the present disclosure provides a method of preparing a hardened dental composition, the method including: providing a hardenable dental composition including a surface treated inorganic dental filler as described herein; and providing conditions effective to harden the hardenable dental composition.

Advantages

Hardened dental compositions that include an inorganic dental filler having a surface treated with at least one (meth)acrylated silane as described herein, can exhibit comparable diametral tensile strengths to known hardened dental compositions, while at the same time advantageously exhibiting up to a 50% lower stress profile compared to other hardened dental compositions. In some embodiments, the surface treated inorganic dental fillers disclosed herein can provide improved wetting and paste handling properties for certain resins.

Definitions

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for compounds of this invention are those that do not interfere with the surface treatment of the inorganic particles. In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tert-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

As used herein, an "alkylene" refers to a divalent radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

As used herein, an "arylene" group refers to a divalent group that is a radical of an aryl group. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

As used herein, an "alkarylene" group refers to a divalent group of formula —Ar—$R^a$ where Ar is an arylene and $R^a$ is an alkyl group.

As used herein, an "aralkylene" group refers to a divalent group of formula —$R^a$—Ar where $R^a$ is an alkylene and Ar is an aryl group.

As used herein, a "dental composition" or a "composition for dental use" or a "composition to be used in the dental field" refers to any composition that can be used in the dental field. In this respect the composition should be not detrimental to the patients' health and thus free of hazardous and toxic components being able to migrate out of the composition. Dental compositions are typically hardenable compositions that can be hardened at ambient conditions, including a temperature range from about 15 to 50° C. or from about 20 to 40° C. within a time frame of about 5 to 40 seconds. Higher temperatures are not recommended as they might cause pain to the patient and may be detrimental to the patient's health. Dental compositions are typically provided to the practitioner in single or multi-dose quantities. For example, a capsule can contain 0.25 g to 0.45 g of the dental composition. A multi-dose syringe can contain, for example, about 4 g of the dental composition.

As used herein, a "polymerizable component" refers to any component that can be cured or solidified, for example, by heating to cause polymerization or chemical crosslinking.

As used herein, the term "resin" refers to a polymerizable component that contains one, two, three, or more polymerizable groups. Exemplary polymerizable groups include, but are not limited to, unsaturated organic groups, such as vinyl groups such as found in a (methyl)acrylate group. A resin can often be cured by radiation induced polymerization or crosslinking, or by using a redox initiator.

As used herein, the term "monomer" refers to any chemical substance that can be characterized by a chemical formula, bearing polymerizable groups (e.g., (meth)acrylate groups) that can be polymerized to oligomers or polymers, thereby increasing the molecular weight. The molecular weight of monomers can typically be calculated from the given chemical formula.

As used herein, "(meth)acryl" is a shorthand term referring to "acryl" and/or "methacryl." For example, a "(meth) acryloxy" group is a shorthand term referring to either an acryloxy group (i.e., $CH_2$=CH—C(O)—O—) and/or a methacryloxy group (i.e., $CH_2$=C($CH_3$)—C(O)—O—).

As used herein, the term "initiator" refers to a substance capable of starting or initiating a curing process for resins or monomers, for example, by a redox/auto-cure chemical reaction, by a radiation induced reaction, or by a heat induced reaction.

As used herein, the term "powder" refers to a dry, bulk solid composed of a large number of very fine particles that may flow freely when shaken or tilted.

As used herein, the term "particle" refers to a substance being a solid having a shape that can be geometrically determined. Particles can typically be analyzed with respect to, for example, grain size or diameter.

The mean particle size of a powder can be obtained from various techniques including laser diffraction particle size analysis. The cumulative curve of the grain size distribution can be obtained and defined as the arithmetic average of the measured grain sizes of a certain powder mixture. Respective measurements can be done using available diffraction laser particle size analyzers such as Beckman Coulter LS 13 320 Laser Diffraction Particle Size Analyzer or granulometers such as CILAS Laser Diffraction Particle Size Analysis Instrument.

As used herein, the term "dX" (micrometers) with respect to particle size measurements means that X % of the particles in the analyzed volume have a size below the indicated value in micrometers. For example, a particle size value of 100 micrometers (d50) means that within the analyzed volume, 50% of the particles have a size below 100 micrometers.

As used herein, the term "paste" refers to a soft, viscous mass of solids dispersed in a liquid.

As used herein, the term "viscous" refers to a material having a viscosity above about 3 Pa*s (at 23° C.).

As used herein, the term "liquid" refers to any solvent or liquid that is able to at least partially disperse or dissolve a component at ambient conditions (e.g., 23° C.). A liquid typically has a viscosity below about 10 or below about 8 or below about 6 Pa*s.

As used herein, a "glass ionomer cement" or a "GIC" refers to a cement capable of curing or hardening by the reaction between an acid-reactive glass and a polyacid in the presence of water.

As used herein, a "resin modified glass ionomer cement" or "RM-GIC" refers to a GIC additionally containing a resin, an initiator system, and typically 2-hydroxylethyl methacrylate (HEMA).

As used herein, a composition is "essentially free of" or "substantially free of" a certain component (e.g., a resin), if the composition does not contain said component as an essential feature. Thus, said component is not intentionally added to the composition either as such or in combination with other components or ingredients of other components.

A composition being essentially free of a certain component (e.g., a resin) usually contains the component in an amount of less than about 5 wt.-%, less than about 1 wt.-%, less than about 0.5 wt.-%, or less than about 0.01 wt.-%, with respect to the total weight of the composition or material. The composition may not contain said component at all. However, sometimes the presence of a small amount of the said component can be unavoidable, for example, due to impurities contained in the raw materials used.

As used herein, an "acid-reactive filler" refers to a filler that can chemically react in the presence of a polyacid leading to a hardening reaction.

As used herein, a "non acid-reactive filler" refers to a filler, that when mixed with a polyacid, (i) does not show a chemical reaction within 6 minutes, or (ii) only shows a reduced (e.g., time-delayed) hardening reaction.

To distinguish an acid-reactive filler from a non acid-reactive filler the following test can or is to be conducted: A composition is prepared by mixing a first part and a second part in a mass ratio of 1 to 3, wherein: the first part contains: poly (acrylic acid-co-maleic acid) (Mw: about 20,000+/−3, 000): 43.6 wt.-%, water: 47.2 wt.-%, tartaric acid: 9.1 wt.-%, and benzoic acid: 0.1 wt.-%; and the second part contains: filler to be analyzed: 100 wt.-%.

The filler is characterized as non acid-reactive, if within 6 minutes after preparing the above composition the shear stress is less than 50,000 Pa determined by conducting an oscillating measurement using a rheometer under the following conditions: using an 8 millimeter plate, 0.75 millimeter gap, at 28° C., frequency: 1.25 Hz, and deformation: 1.75%.

As used herein "nanosilica" is used synonymously with "nano-sized silica particles," and refers to silica particles having an average size of at most 200 nanometers. As used herein for a spherical particle, "size" refers to the diameter of the particle. As used herein for a non-spherical particle, "size" refers to the longest dimension of the particle.

As used herein, the term "silica sol" refers to a stable dispersion of discrete, amorphous silica particles in a liquid, typically water.

As used herein, the terms "pyrogenic silica" and "fumed silica" are used interchangeably and refer to amorphous silicas formed in the vapor phase. Pyrogenic silica may contain, for example, a few hundred primary particles fused into branched-chain, three-dimensional aggregates. Examples of pyrogenic silica include products available under the trade designations AEROSIL OX-50, AEROSIL-130, AEROSIL-150, and AEROSIL-200 available from DeGussa AG, (Hanau, Germany) and CAB-O-SIL M5 available from Cabot Corp (Tuscola, Ill.).

As used herein, "non-pyrogenic silica" refers to amorphous silica that is not formed in the vapor phase. Examples of non-pyrogenic silicas include precipitated silicas and silica gels.

As used herein, "silane treated" means that the surface of a particle has been modified by application of a silane.

As used herein, "aggregated silica" is descriptive of an association of primary silica particles often bound together by, for example, residual chemical treatment, covalent chemical bonds, or ionic chemical bonds. Although complete breakdown of aggregated silica into smaller entities may be difficult to achieve, limited or incomplete breakdown may be observed under conditions including, for example, shearing forces encountered during dispersion of the aggregated silica in a liquid.

As used herein a "cation reduced aluminosilicate glasses" refers to a glass having a lower content of cations in the surface region of the glass particle compared with the inner region of the glass particle. Such glasses typically react much slower upon contact with a solution of polyacrylic acid in water as compared to typical acid-reactive fillers. Examples of non acid-reactive fillers include quartz glass or strontium oxide based glasses. Further examples are described herein. Cation reduction can be achieved by a surface treatment of the glass particles. Useful surface treatments include, but are not limited to, acid washing (e.g., treatment with a phosphoric acid), treatment with a phosphate, treatment with a chelating agent such as tartaric acid, and treatment with a silane or an acidic or basic silanol solution.

As used herein, the terms "polyacid" and/or "polyalkenoic acid" refer to polymers having a plurality of acidic repeating units (e.g., more than 10 or more than 20 or more than 50). That is, the acidic repeating units are attached to or pending from the backbone of the polymer.

As used herein, the phrase "complexing agent" refers to a low molecular agent capable of forming a complex with metal ions such as, for example, calcium and/or magnesium. An exemplary complexing agent is tartaric acid.

As used herein, the terms "hardenable" and/or "curable" refer to compositions that can be cured or solidified, for example, by chemical cross-linking and/or radiation-induced polymerization or crosslinking and/or by conducting a glass ionomer cement reaction.

As used herein, the phrase "ambient conditions" refers to conditions to which dental compositions as described herein are typically subjected during storage and handling. Ambient conditions may include, for example, a pressure of about 900 mbar to about 1100 mbar, a temperature of about $-10°$ C. to about 60° C., and/or a relative humidity of about 10% to about 100%. In the laboratory ambient conditions are typically adjusted to about 23° C. and about 1 atmosphere (e.g., 0.95 to 1.05 atmosphere). In the dental and orthodontic field ambient conditions are reasonably understood to include, for example, a pressure of about 950 mbar to about 1050 mbar, a temperature of about 15° C. to about 40° C., and/or a relative humidity of about 20% to about 80%.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one."

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and in certain situations by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Also, as used herein in connection with a measured quantity, the term "approximately" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

In one aspect, the present disclosure provides an inorganic dental filler including a surface treated with at least one silane.

In one embodiment, the at least one silane is of the formula:

$(R^{Si})$—$(CR^1R^2)_n$—$(NH$—$C(O)$—$O$—$CH_2$—$CH_2)_q$—
$N(R^5)$—$C(O)$—$NH$—$(CH_2$—$CH_2$—$O)$—
$CR^3R^4$—$CH_2$-(A) 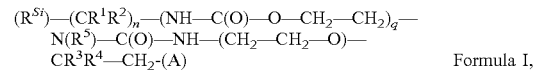

wherein: $R^{Si}$ is a silane-containing group of the formula —$Si(Y_p)(R^6)_{3-p}$, wherein Y is a hydrolysable group, $R^6$ is a monovalent alkyl or aryl group (e.g., an alkyl or aryl moiety), and p is 1, 2, or 3; each $R^1$, $R^2$, and $R^3$ is independently H, an alkyl group (e.g., an alkyl moiety), an aryl group (e.g., an aryl moiety), an alkaryl group (e.g., an alkaryl moiety), or an aralkyl group (e.g., an aralkyl moiety); $R^4$ is H, an alkyl group (e.g., an alkyl moiety), an aryl group (e.g., an aryl moiety), an alkaryl group (e.g., an alkaryl moiety), an aralkyl group (e.g., an aralkyl moiety), or a group or moiety of the formula —$(CH_2)_m$-(A), wherein m is 1 to 6; n is 1 to 6; q is 0 or 1; t is 0 or 1; A is a (meth)acryl group of the formula $X^1$—$C(O)$—$C(R^7)$=$CH_2$, wherein $X^1$ is —O, —S, or —$NR^7$, and each $R^7$ is independently H or a $C_1$-$C_4$ alkyl group or moiety; and $R^5$ is H, an alkyl group (e.g., an alkyl moiety), a cycloalkyl group (e.g., a cycloalkyl moiety), an aryl group (e.g., an aryl moiety), an alkaryl group (e.g., an alkaryl moiety), an aralkyl group (e.g., an aralkyl moiety), a group or moiety of the formula $(R^{Si})$—

$(CR^1R^2)_n$—NH—C(O)—O—CH$_2$—CH$_2)_q$—, a group or moiety of the formula $(R^{Si})$—$(CR^1R^2)_n$—NH—C(O)—N$(R^8)$—(CH$_2)_m$—, a group or moiety of the formula —(CH$_2)_m$-(A), a group or moiety of the formula —(CH$_2)_m$—N(R')—C(O)—NH—(CH$_2$—CH$_2$—O)$_t$—CR$^3$R$^4$—CH$_2$-(A), or a group or moiety of the formula —(CH$_2)_m$—N(R')—C(O)—NH—R$^9$; wherein each m and n is independently 1 to 6, q is 0 or 1, t is 0 or 1, and each R$^1$, R$^2$, R$^3$, R$^4$, R$^{Si}$, and A are as defined above; R$^8$ is H or a group or moiety of the formula —(CH$_2)_m$—NH—C(O)—NH—(CH$_2$—CH$_2$—O)$_t$—CR$^3$R$^4$—CH$_2$-(A), a group of the formula —(CH$_2)_m$—NH—C(O)—NH—(CR$^1$R$^2)_n$—(R$^{Si}$), or a group of the formula —(CH$_2)_m$—NH—C(O)—NH—R$^9$, wherein each m and n is independently 1 to 6, t is 0 or 1, and each R$^1$, R$^2$, R$^3$ R$^4$, R$^{Si}$, and A are as defined above; and R$^9$ is an alkyl group (e.g., an alkyl moiety), an aryl group (e.g., an aryl moiety), an alkaryl group (e.g., an alkaryl moiety), or an aralkyl group (e.g., an aralkyl moiety); with the proviso that at least one of R$^1$, R$^2$, R$^3$, R$^4$, and R$^5$ is not H.

In some embodiments of Formula I, each R$^1$, R$^2$, and R$^3$ is independently H or CH$_3$.

In some embodiments of Formula I, R$^4$ is H, CH$_3$, or a group or moiety of the formula —(CH$_2)_m$-(A), wherein m is 1.

In some embodiments of Formula I, q is 0.
In some embodiments of Formula I, t is 0.
In some embodiments of Formula I, n is 1 to 3.
In some embodiments of Formula I, A is —O—C(O)—CH=CH$_2$ or —O—C(O)—C(CH$_3$)=CH$_2$.
In some embodiments of Formula I, R$^8$ is H.
In some embodiments of Formula I, R$^9$ is a phenyl group or moiety.
In some embodiments of Formula I, R$^{Si}$ is —Si(OCH$_3$)$_3$ or —Si(OCH$_2$CH$_3$)$_3$.

In certain embodiments, the silane is a structural isomer related to Formula I. Exemplary structural isomers related to Formula I include, but are not limited to silanes of the formulas:

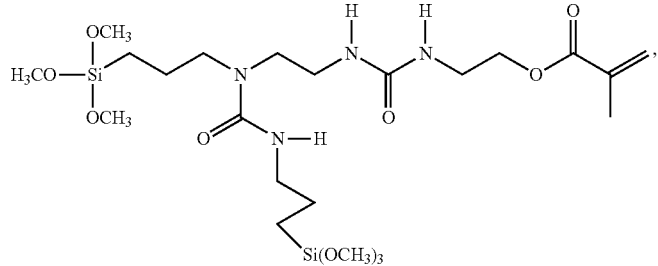

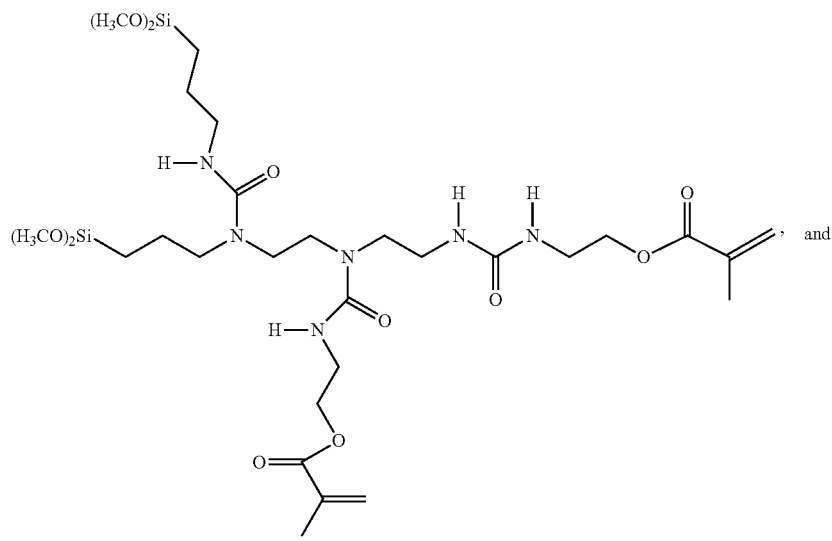

, and

-continued

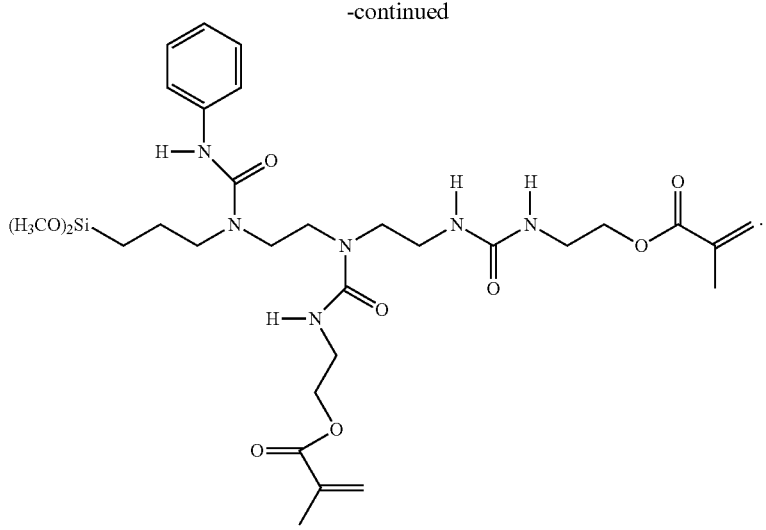

In another embodiment, the at least one silane is of the formula:

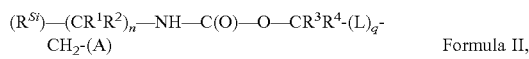
                                                  Formula II, wherein: $R^{Si}$ is a silane-containing group of the formula —$Si(Y_p)(R^6)_{3-p}$, wherein Y is a hydrolysable group, $R^6$ is a monovalent alkyl or aryl group (e.g., an alkyl or aryl moiety), and p is 1, 2, or 3; each $R^1$, $R^2$, and $R^3$ is independently H, an alkyl group (e.g., an alkyl moiety), an aryl group (e.g., an aryl moiety), an alkaryl group (e.g., an alkaryl moiety), or an aralkyl group (e.g., an aralkyl moiety); $R^4$ is H, an alkyl group (e.g., an alkyl moiety), an aryl group (e.g., an aryl moiety), an alkaryl group (e.g., an alkaryl moiety), or an aralkyl group (e.g., an aralkyl moiety), wherein the group may optionally be substituted with one or more catenary oxygen atoms, —O—C(O)— groups, and/or —C(O)—O— groups; n is 1 to 6; q is 0 or 1; L is a divalent alkylene group (e.g., an alkylene moiety), a divalent arylene group (e.g., an arylene moiety), a divalent alkarlyene group (e.g., an alkarylene moiety), or a divalent aralkylene group (e.g., an aralkylene moiety), wherein the divalent group may optionally be substituted with one or more catenary oxygen atoms, —O—C(O)— groups, and/or —C(O)—O— groups; and A is a (meth)acryl group of the formula $X^1$—C(O)—C($R^7$)=$CH_2$, wherein $X^1$ is —O, —S, or —$NR^7$, and each $R^7$ is independently H or a $C_1$-$C_4$ alkyl group (e.g., alkyl moiety); with the proviso that at least one of $R^1$, $R^2$, $R^3$, and $R^4$ is not H.

In some embodiments of Formula I, each $R^1$, $R^2$, and $R^3$ is independently H or $CH_3$.

In some embodiments of Formula II, $R^4$ is H, $CH_3$, or a group or moiety of the formula —$(CH_2)_m$-(A), wherein m is 1.

In some embodiments of Formula II, q is 0.

In some embodiments of Formula II, n is 1 to 3.

In some embodiments of Formula II, A is —O—C(O)—CH=$CH_2$ or —O—C(O)—C($CH_3$)=$CH_2$.

In some embodiments of Formula II, $R^{Si}$ is —$Si(OCH_3)_3$ or —$Si(OCH_2CH_3)_3$.

In some embodiments of Formula II, L is

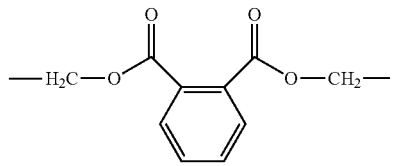

In some embodiments of Formula II, $R^4$ is —$CH_2$—O—C(O)-Ph.

In some embodiments of the surface treated inorganic dental filler, the inorganic dental filler is selected from the group consisting of non-agglomerated particles, agglomerated particles, non-aggregated particles, aggregated particles, clusters, and combinations thereof.

Inorganic Fillers

In some embodiments of the surface treated inorganic dental filler, the inorganic dental filler is a non acid-reactive filler.

In some embodiments of the surface treated inorganic dental filler, the inorganic dental filler includes nano-particles.

In some embodiments of the surface treated inorganic dental filler, the inorganic dental filler includes clusters of nano-particles. Clusters of nano-particles may be formed from a combination of non-heavy metal oxide and/or heavy metal oxide, for example as disclosed in U.S. Pat. No. 6,730,156 (Windisch et al.).

In some embodiments of the surface treated inorganic dental filler, the inorganic dental filler includes metal oxide particles.

In some embodiments of the surface treated inorganic dental filler, the inorganic dental filler includes silica particles, zirconia particles, titania particles, aluminosilicate glasses, doped aluminosilicate glasses, or combinations thereof. Doped aluminosilicate glasses include, for example, barium aluminosilicates, strontium aluminosilicates, lanthanum aluminosilicates, and combinations thereof.

In some embodiments of the surface treated inorganic dental filler, the inorganic dental filler includes particles having an average particle size of 5 nanometers to 20 microns. In certain embodiments of the surface treated inorganic dental filler, the inorganic dental filler includes particles having an average particle size of 5 nanometers to 10 microns. In some certain embodiments of the surface treated inorganic dental filler, the inorganic dental filler includes particles having an average particle size of 5 nanometers to 0.4 microns.

In some embodiments of the surface treated inorganic dental filler, the particles have at least 25% surface coverage of the particles with the at least one silane.

Non Acid-Reactive Fillers

In some embodiments of the surface treated inorganic dental filler, the inorganic filler can be a non acid-reactive filler. A non acid-reactive filler is a filler that when combined with a polyacid in the presence of water either (i) does not cure in a glass ionomer cement reaction at all, or (ii) that only shows a delayed curing reaction.

A wide variety of non acid-reactive fillers can be used in the hardenable dental compositions disclosed herein. In certain embodiments, the non acid-reactive filler is an inorganic filler. In certain embodiments, the non acid-reactive filler is non-toxic and suitable for use in the mouth of a human being. A non acid-reactive filler can be radiopaque or radiolucent.

In certain embodiments, the non acid-reactive filler can include quartz, nitrides, kaolin, borosilicate glass, strontium oxide based glass, barium oxide based glass, silica, alumina, titania, zirconia, or a combination thereof.

In certain embodiments, the non acid-reactive filler can include a metal oxide such as alumina, silica, zirconia, titania, or a combination thereof. In some embodiments the metal oxide can further include modifiers or dopants such as sodium, magnesium, lithium, calcium, strontium, barium, yttrium, ytterbium, lanthanum, zinc, iron, manganese, bismuth oxides, or a combination thereof.

In certain embodiments, the non acid-reactive filler has a mean particle size of 0.005 micrometer to 20 micrometers. For some embodiments, the non acid-reactive filler has a mean particle size of 0.01 micrometer to 10 micrometers. In certain embodiments, the non acid-reactive filler has a d50 of less than 10 micrometers. For embodiments in which both the first paste and the second paste include a non acid-reactive fillers, the mean particle size of the non acid-reactive filler in the second paste can be the same or different than the mean particle size of the non acid-reactive filler in the first paste.

Exemplary non acid-reactive filler are further described, for example, in International Application Publication No. WO 2017/015193 A1 (Jahns et al.).

Nano-Sized Silica Particles

In some embodiments of the surface treated inorganic dental filler, the inorganic filler can include non-aggregated, nano-sized silica particles. In some embodiments, the non-aggregated, nano-sized silica particles are substantially free of fumed silica (i.e., pyrogenic silica). However pyrogenic fillers (e.g., fumed silica) can be added as optional additives to the dental compositions.

A wide variety of non-aggregated, nano-sized silica particles can be surface treated as described herein. In some embodiments, the non-aggregated, nano-sized silica particles are available as a silica sol. In certain embodiments, the starting silica sol can be, for example, NALCO 1034A, NALCO 1042, NALCO 2327, NALCO 2329 or LEVASIL 50/50.

Exemplary non-aggregated, nano-sized silica particles include those available from Nalco Chemical Co. (Naperville, Ill.) under the product designation NALCO COLLOIDAL SILICAS (e.g., NALCO products 1034A, 1040, 1042, 1050, 1060, 2327, and 2329), Nissan Chemical America Company, Houston, Tex. (e.g., SNOWTEX-ZL, -OL, -O, -N, -C, -20L, -40, and -50); Admatechs Co., Ltd., Japan (e.g., SX009-MIE, SX009-MIF, SC1050-MJM, and SC1050-MLV); Grace GmbH & Co. KG, Worms, Germany (e.g., those available under the product designation LUDOX, e.g., P-W50, P-W30, P-X30, P-T40 and P-T40AS); Akzo Nobel Chemicals GmbH, Leverkusen, Germany (e.g., those available under the product designation LEVASIL, e.g., 50/50, 100/45, 200/30%, 200A/30, 200/40, 200A/40, 300/30 and 500/15), and Bayer Material Science AG, Leverkusen, Germany (e.g., those available under the product designation DISPERCOLL S, e.g., 5005, 4510, 4020 and 3030). Further exemplary fillers including non-aggregated, nano-sized silica particles and methods of preparing the fillers are disclosed in, for example, International Publication No. WO 01/30307 (Craig et al.).

For embodiments in which the dental composition further includes pyrogenic fillers (e.g., fumed silica), a wide variety of pyrogenic fillers such as fumed silica can be used. Exemplary fumed silicas include for example, products sold under the trade designations AEROSIL series OX-50, -130, -150, and -200, Aerosil R8200 available from Degussa AG, (Hanau, Germany), CAB-O-SIL M5 available from Cabot Corp (Tuscola, Ill.), and HDK types, e.g. HDK-H 2000, HDK H15; HDK H18, HDK H20 and HDK H30 available from Wacker.

In one embodiment, the non-aggregated, nano-sized silica particles have an average particle size of at most about 200 nanometers, in some embodiments at most about 150 nanometers, and in certain embodiments at most about 120 nanometers. In one embodiment, the non-aggregated, nano-sized silica particles have an average particle size of at least about 5 nanometers, in some embodiments at least about 20 nanometers, and in certain embodiments at least about 50 nanometers. These measurements can be based on a TEM (transmission electron microscopy) method, whereby a population of particles is analyzed to obtain an average particle size.

An exemplary method for measuring the particle diameter can be described is as follows: Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 Kv. A population size of about 50-100 particles can be measured and an average diameter can be determined.

In one embodiment, the average surface area of the non-aggregated, nano-sized silica particles is at least about 15 $m^2/g$, and in some embodiments at least about 30 $m^2/g$.

In some embodiments, the non-aggregated, nano-sized silica particles are substantially spherical and substantially non-porous. Although the silica may be essentially pure in certain embodiments, it may contain small amounts of stabilizing ions such as ammonium and alkaline metal ions in other embodiments.

Surface Treatment of Inorganic Fillers

In another aspect, the present disclosure provides a method of preparing a surface treated inorganic dental filler as disclosed herein, the method including contacting an inorganic filler with at least one silane of Formula I or Formula II as described herein.

In some embodiments, the method includes contacting the inorganic filler with the at least one silane in a liquid medium.

In certain embodiments, the liquid medium includes at least one organic solvent. In some certain embodiments, the at least one organic solvent is selected from the group consisting of alcohols (e.g., ethanol), acetates (e.g., ethyl acetate), aromatics (e.g., toluene), ketones (e.g., methyl ethyl ketone), and combinations thereof.

In some embodiments, the liquid medium further includes water.

In some embodiments, the liquid medium further includes at least one catalyst. In certain embodiments, the catalyst is an acidic catalyst or a basic catalyst.

A wide variety of acidic catalysts can be used including, for example, organic acidic catalysts and inorganic acidic catalysts. In certain embodiments, the acidic catalyst is at least partially soluble, and in certain embodiments completely soluble, at the selected concentration in the liquid medium being used.

Exemplary organic acidic catalysts include, but are not limited to, carboxylic acids, sulfonic acids, phosphonic acids, and combinations thereof.

Exemplary inorganic acidic catalysts include, but are not limited to, hydrochloric acid, nitric acid, sulfuric acid, phosphoric acid, antimonic acid, boric acid, and combinations thereof.

A wide variety of basic catalysts can also be used including, for example, organic basic catalysts and inorganic basic catalysts. In certain embodiments, the basic catalyst is at least partially soluble, and in certain embodiments completely soluble, at the selected concentration in the liquid medium being used.

Exemplary organic basic catalysts include, but are not limited to, amines including, for example, primary amines, secondary amines, tertiary amines, and combinations thereof.

Exemplary inorganic basic catalysts include, but are not limited to, sodium hydroxide, potassium hydroxide, calcium hydroxide, ammonium hydroxide, and combinations thereof.

In some embodiments, contacting includes stirring or mixing the inorganic filler and the at least one silane in the liquid medium. In some embodiments, the method further includes removing at least a portion of the liquid medium to provide a dry inorganic dental filler including a surface treated with the at least one silane. In some certain embodiments, removing the liquid medium includes a process selected from the group consisting of heating, reducing pressure, freeze drying, and combinations thereof.

Hardenable Dental Compositions

In another aspect, the present disclosure provides a hardenable dental composition that includes a surface treated inorganic dental filler as disclosed herein. In some embodiments, the hardenable dental composition further includes at least one polymerizable resin. In certain embodiments, the at least one polymerizable resin is a free radically polymerizable resin. In some embodiments, the hardenable dental composition further includes additional surface treated and/or non-surface treated inorganic fillers. In some embodiments, the hardenable dental composition further includes an initiator system. In certain embodiments, the initiator system is selected from the group consisting of photoinitiator systems, redox initiator systems, peroxide heat activated initiator systems, and combinations thereof.

In some embodiments, the hardenable dental composition can include 10 wt.-% to 90 wt.-% of the surface treated inorganic dental filler as disclosed herein, based on the total weight of the dental composition. In some embodiments, the hardenable dental composition can include 30 wt.-% to 90 wt.-% of the surface treated inorganic dental filler as disclosed herein, based on the total weight of the dental composition.

In some embodiments, the hardenable dental composition is a single part dental composition or a multi-part dental composition.

Polymerizable Resins

Polymerizable resins are materials having free radically active functional groups and include monomers, oligomers, and polymers having one or more ethylenically unsaturated groups. Suitable materials contain at least one ethylenically unsaturated bond, and are capable of undergoing addition polymerization.

Free radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200-500, copolymerizable mixtures of acrylated monomers such as those in U.S. Pat. No. 4,652,274 (Boettcher et al.), and acrylated oligomers such as those of U.S. Pat. No. 4,642,126 (Zador et al.); and vinyl compounds such as styrene, diallyl phthalate, divinyl succinate, divinyladipate and divinylphthalate. Mixtures of two or more of these free radically polymerizable materials can be used if desired. Suitable polymerizable polymers include, for example, partially or fully acrylate- or methacrylate-functionalized polymers including, for example, functionalized poly(acrylic acid) polymers, cellulosics, poly(vinylalcohol) polymers, poly(oxyethylene)-poly(oxypropylene) block copolymers, poly(ethyleneglycol) polymers, and combinations thereof.

In certain embodiments, the hardenable dental composition can include 10 wt.-% to 90 wt.-% free radically polymerizable resin, based on the total weight of the hardenable dental composition. In certain embodiments, the hardenable dental composition can include 15 wt.-% to 60 wt.-% free radically polymerizable resin, based on the total weight of the hardenable dental composition. In some embodiments, the hardenable dental composition can include 15 wt.-% to 40 wt.-% free radically polymerizable resin, based on the total weight of the hardenable dental composition.

Initiator Systems

For free radical polymerization (hardening), an initiation system can be selected from systems which initiate polymerization via radiation, heat, or redox/auto-cure chemical reaction.

A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 800 nm.

For certain embodiments the free radical initiator system can include a photoinitiator system. One type of suitable initiator (i.e., initiator system) is described in U.S. Pat. No. 5,545,676 (Palazzotto et al.), which includes a three component or ternary photoinitiator system. This system includes an iodonium salt, e.g., a diaryliodonium salt, which can be a simple salt (e.g., containing an anion such as Cl$^-$, Br$^-$, I$^-$, or $C_2H_5SO_3^-$) or a metal complex salt (e.g., containing $SbF_5OH^-$ or $AsF_6^-$). Mixtures of iodonium salts can be used if desired. The second component in this ternary photoinitiator system is a sensitizer, which is capable of light absorption within the range of wavelengths of about 400 nm to about 1200 nm. The third component in this ternary photoinitiator system is an electron donor and includes amines (including aminoaldehydes and aminosilanes or other amines as described for the first initiator system), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid.

Examples of sensitizers suitable for use in a ternary photoinitiator system include ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes, and pyridinium dyes. In some embodiments, the sensitizers are ketones (e.g., monoketones or alpha-diketones), ketocoumarins, aminoarylketones, p-substituted aminostyryl ketone compounds, or combinations thereof. Exemplary visible light sensitizers include camphorquinone, glyoxal, biacetyl, 3,3,6,6-tetramethylcyclohexanedione, 3,3,7,7-tetramethyl-1,2-cycloheptanedione, 3,3,8,8-tetramethyl-1,2-cyclooctanedione, 3,3,18,18-tetramethyl-1,2-cyclooctadecanedione, dipivaloyl, benzil, furil, hydroxybenzil, 2,3-butanedione, 2,3-pentanedione, 2,3-hexanedione, 3,4-hexanedione, 2,3-heptanedione, 3,4-heptanedione, 2,3-octanedione, 4,5-octanedione, 1,2-cyclohexanedione, and combinations thereof. In certain embodiments, the sensitizer is camphorquinone.

In some embodiments, visible light-induced initiators include camphorquinone combined with a suitable hydrogen donor (e.g., an amine such as those described above for the first initiator system), and optionally a diaryliodonium simple or metal complex salt, chromophore-substituted halomethyl-s-triazine, or halomethyl oxadiazole. In certain embodiments, visible light-induced photoinitiators include combinations of an alpha-diketone (e.g., camphorquinone) with additional hydrogen donors, and optionally a diaryliodonium salt (e.g., diphenyliodonium chloride, bromide, iodide or hexafluorophosphate).

In some embodiments, ultraviolet light-induced polymerization initiators include ketones, such as benzyl and benzoin, acyloins, and acyloin ethers. In certain embodiments, ultraviolet light-induced polymerization initiators include 2,2-dimethoxy-2-phenylacetophenone available under the trade designation IRGACURE 651 and benzoin methyl ether (2-methoxy-2-phenylacetophenone), both from Ciba Specialty Chemicals Corp., Tarrytown, N.Y.

Various other initiators are known in the art, such as described in U.S. Pat. No. 7,674,850 (Karim et al.) and U.S. Pat. No. 7,816,423 (Karim et al.).

The initiator system is present in an amount sufficient to provide the desired rate of hardening (e.g., polymerizing and/or crosslinking). For a photoinitiator, this amount will be dependent in part on the light source, the thickness of the layer to be exposed to radiant energy, and the extinction coefficient of the photoinitiator. In some embodiments the initiator system is present in a total amount of at least about 0.01 wt.-%, in certain embodiments at least about 0.03 wt.-%, and in some certain embodiments at least about 0.05 wt.-%, based on the weight of the hardenable dental composition. In some embodiments the initiator system is present in a total amount of no more than about 10 wt.-%, in certain embodiments no more than about 5 wt.-%, and in some certain embodiments no more than about 2.5 wt.-%, based on the weight of the hardenable dental composition.

A redox initiator system includes redox agents. The redox agents may include an oxidizing agent and a reducing agent. Suitable polymerizable components, redox agents, optional acid-functional components, and optional fillers that are useful in the present invention are described in U.S. Pat. No. 7,173,074 (Mitra et al.) and U.S. Pat. No. 6,982,288 (Mitra et al.). Alternatively, the redox agents may include a free-radical initiator system containing enzymes as disclosed in U.S. Patent Application Pub. No. 2004/0122126 A1 (Wu et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. In at least some embodiments, the reducing and oxidizing agents are sufficiently shelf-stable and free of undesirable colorization to permit their storage and use under typical dental conditions.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. In certain embodiments the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments a secondary ionic salt may be included to enhance the stability of the polymerizable composition as described in U.S. Pat. No. 6,982,288 (Mitra et al.).

The reducing and oxidizing agents are present in amounts sufficient to permit an adequate free-radical reaction rate. This can be evaluated by combining all of the ingredients of the polymerizable composition except for any optional filler, and observing whether or not a hardened mass is obtained.

The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-immiscible encapsulant, the reducing and oxidizing agents can be combined with an FAS glass and water and maintained in a storage-stable state.

A redox cure system can be combined with other cure systems, e.g., with a glass ionomer cement and with a photopolymerizable composition such as described U.S. Pat. No. 5,154,762 (Mitra et al.).

The hardenable compositions that utilize a redox cure system can be supplied in a variety of forms including two-part powder/liquid, paste/liquid, and paste/paste systems. Other forms employing multi-part combinations (i.e., combinations of two or more parts), each of which is in the form of a powder, liquid, gel, or paste are also possible. In a multi-part system, one part typically contains the reducing agent(s) and another part typically contains the oxidizing agent(s). Therefore, if the reducing agent is present in one part of the system, then the oxidizing agent is typically present in another part of the system. However, the reducing agent and oxidizing agent can be combined in the same part of the system through the use of the microencapsulation technique.

Optional Additives

The hardenable dental compositions disclosed herein may optionally include various additives known in the art including, but not limited to, flavorants, fluoridating agents, buffering agents, numbing agents, remineralization agents, desensitization agents, colorants, indicator(s), viscosity modifiers, surfactants, stabilizers, preservative agents (e.g., benzoic acid), or combinations thereof. The presence of a colorant can aid in detecting that the aqueous composition has coated all the desired intraoral surfaces. The intensity of a colorant can also aid in detecting the uniformity of the coating on the intraoral surfaces.

For embodiments of the hardenable dental compositions disclosed herein in which an additive is present in the hardenable dental composition, the hardenable dental composition includes at least 0.01 wt.-% additive, at least 0.05 wt.-% additive, or at least 0.1 wt.-% additive, based on the total weight of the hardenable dental composition For embodiments of the hardenable dental compositions disclosed herein in which an additive is present in the hardenable dental composition, the hardenable dental composition includes at most 5 wt.-% additive, at most 3 wt.-% additive, or at most 1 wt.-% additive, based on the total weight of the hardenable dental composition.

Methods, Devices, and Hardened Compositions

In another aspect, the present disclosure provides a method of preparing a hardened dental composition, the method including: providing a hardenable dental composition including a surface treated inorganic dental filler as described herein; and providing conditions effective to harden the dental composition. In some embodiments, conditions effective to harden the dental composition include a process selected from the group consisting of heating, irradiating, combining parts of a multi-part hardenable dental composition, vacuum starvation, and combinations thereof.

The hardenable dental composition disclosed herein may be hardened by inducing the polymerizable component to polymerize. For example, polymerization may be induced by the application of actinic radiation. In certain embodiments, the composition is irradiated with radiation having a wavelength of 400 to 1200 nanometers, and in certain embodiments with visible radiation. Visible light sources include, for example, the sun, lasers, metal vapor (e.g., sodium and mercury) lamps, incandescent lamps, halogen lamps, mercury arc lamps, fluorescent room light, flashlights, light emitting diodes, tungsten halogen lamps, and xenon flash lamps.

In some embodiments, the hardenable dental composition can be a multi-part dental composition (e.g., a two-part dental composition). For example, components of a redox initiator system may be contained in separate parts. For multi-part dental compositions, the multiple parts can be provided to the practitioner in various embodiments.

In one embodiment, the multiple parts may be contained in separate sealable vessels (e.g., made out of plastic or glass). For use, the practitioner may take adequate portions of the components from the vessels and mix the portions by hand on a mixing plate.

In some embodiments, the multiple parts are contained in separate compartments of a storage device. The storage device typically includes two compartments for storing the respective parts, each compartment being equipped with a nozzle for delivering the respective parts. Once delivered in adequate portions, the parts can then be mixed by hand on a mixing plate.

In certain embodiments, the storage device has an interface for receiving a static mixing tip. The mixing tip is used for mixing the respective parts. Static mixing tips are available from, for example, SulzerMixpac Company. Useful storage devices include cartridges, syringes, and tubes.

The storage device typically includes two housings or compartments having a front end with a nozzle and a rear end and at least one piston movable in the housing or compartment.

Useful cartridges are described, for example, in U.S. Patent Application Pub. No. 2007/0090079 A1 (Keller et al.) and U.S. Pat. No. 5,918,772 (Keller et al.). Useful cartridges are available from, for example, SulzerMixpac AG (Switzerland). Useful static mixing tips are described, for example, in U.S. Patent Application Pub. No. 2006/0187752 A1 (Keller et al.) and in U.S. Pat. No. 5,944,419 (Streiff). Useful mixing tips are available from, for example, SulzerMixpac AG (Switzerland).

Other useful storage devices are described, for example, in WO 2010/123800 (3M), WO 2005/016783 (3M), WO 2007/104037 (3M), WO 2009/061884 (3M).

Alternatively, multi-part hardenable dental compositions as described herein can be provided in individual syringes and the individual pastes can be mixed by hand prior to use.

In certain embodiments, a multi-part hardenable dental composition as disclosed herein can be provided as a kit that includes the multiple parts, and instructions describing one or more methods (as disclosed herein) for mixing the multiple parts to form a cured composition.

In one embodiment, the present disclosure provides a device for storing a multi-part (e.g., two-part) hardenable dental composition as described herein. The device includes: a first compartment containing the first part; and a second compartment containing the second part. In some embodiments, both the first compartment and the second compartment each independently include a nozzle or an interface for receiving an entrance orifice of a static mixing tip.

In some embodiments, the mixing ratio of first part and the second part is 1:3 to 2:1 with respect to volume, and in certain embodiments, 1:2 to 2:1 with respect to volume.

In other embodiments, the mixing ratio of first part and the second part is 1:6 to 1:1 with respect to weight, and in certain embodiments 1:4 to 1:1 with respect to weight.

The composition obtained or obtainable when mixing the respective parts is in particular useful for producing a dental cement, dental filling material, dental core buildup material or as dental root channel filling material.

In certain embodiments, the mixture (e.g., hardenable composition) is applied to the surface of hard dental tissue, and the mixture (e.g., hardenable composition) is allowed to cure and form a cured composition on the surface of the hard dental tissue.

In another aspect, the present disclosure provides a hardened dental composition including a surface treated inorganic dental filler as described herein. In some embodiments, the hardened dental composition further includes additional surface treated and/or non-surface treated inorganic fillers.

In some embodiments, the hardened dental composition has a CUSP value with an absolute value of no more than 8 microns, and in certain embodiments no more than 6 microns.

In some embodiments, the hardened dental composition has a DTS of at least 60 MPa, and in some embodiments at least 70 MPa.

ILLUSTRATIVE EMBODIMENTS OF THE PRESENT DISCLOSURE

Various embodiments are disclosed that can provide surface treated inorganic fillers and methods of making and using same.

Embodiment 1A is a surface treated inorganic dental filler comprising a surface treated with at least one silane of the formula:

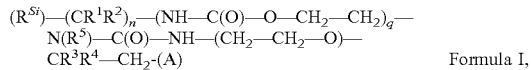

Formula I, wherein: $R^{Si}$ is a silane-containing group of the formula —$Si(Y_p)(R^6)_{3-p}$, wherein Y is a hydrolysable group, $R^6$ is a monovalent alkyl or aryl group, and p is 1, 2, or 3; each $R^1$, $R^2$, and $R^3$ is independently H, an alkyl group, an aryl group, an alkaryl group, or an aralkyl group; $R^4$ is H, an alkyl group, an aryl group, an alkaryl group, an aralkyl group, or a group of the formula —$(CH_2)_m$-(A), wherein m is 1 to 6; n is 1 to 6; q is 0 or 1; t is 0 or 1; A is a (meth)acryl group of the formula $X^1$—C(O)—C($R^7$)=$CH_2$, wherein $X^t$ is —O, —S, or —$NR^7$, and each $R^7$ is independently H or a $C_1$-$C_4$ alkyl group; and $R^5$ is H, an alkyl group, a cycloalkyl group, an aryl group, an alkaryl group, an aralkyl group, a group of the formula ($R^{Si}$)—($CR^1R^2$)$_n$—(NH—C(O)—O—$CH_2$—$CH_2$)$_q$—, a group of the formula ($R^{Si}$)—($CR^1R^2$)$_n$—NH—C(O)—N($R^8$)—($CH_2$)$_m$—, a group of the formula —$(CH_2)_m$-(A), a group of the formula —$(CH_2)_m$—N($R^8$)—C(O)—NH—($CH_2$—$CH_2$—O)$_t$—$CR^3R^4$—$CH_2$-(A), or a group of the formula —$(CH_2)_m$—N(R')—C(O)—NH—$R^9$; wherein each m and n is independently 1 to 6, q is 0 or 1, t is 0 or 1, and each $R^1$, $R^2$, $R^3$, $R^4$, $R^{Si}$, and A are as defined above; $R^8$ is H or a group of the formula —$(CH_2)_m$—NH—C(O)—NH—($CH_2$—$CH_2$—O)$_t$—$CR^3R^4$—$CH_2$-(A), a group of the formula —$(CH_2)_m$—NH—C(O)—NH—($CR^1R^2$)$_n$—($R^{Si}$), or a group of the formula —$(CH_2)_m$—NH—C(O)—NH—$R^9$, wherein each m and n is independently 1 to 6, t is 0 or 1, and each $R^1$, $R^2$, $R^3$ $R^4$, $R^{Si}$, and A are as defined above; and $R^9$ is an alkyl group, an aryl group, an alkaryl group, or an aralkyl group; with the proviso that at least one of $R^1$, $R^2$, $R^3$, $R^4$, and $R^5$ is not H.

Embodiment 2A is a surface treated inorganic dental filler of embodiment 1A, wherein t is 0.

Embodiment 3A is a surface treated inorganic dental filler of embodiment 1A or 2A, wherein each $R^1$, $R^2$, and $R^3$ is independently H or $CH_3$.

Embodiment 4A is a surface treated inorganic dental filler of any one of embodiments 1A to 3A, wherein $R^4$ is H, $CH_3$, or a group of the formula —$(CH_2)_m$-(A), wherein m is 1.

Embodiment 5A is a surface treated inorganic dental filler of any one of embodiments 1A to 4A, wherein q is 0.

Embodiment 6A is a surface treated inorganic dental filler of any one of embodiments 1A to 5A, wherein n is 1 to 3.

Embodiment 7A is a surface treated inorganic dental filler of any one of embodiments 1A to 6A, wherein A is —O—C(O)—CH=$CH_2$ or —O—C(O)—C($CH_3$)=$CH_2$.

Embodiment 8A is a surface treated inorganic dental filler of any one of embodiments 1A to 7A, wherein $R^8$ is H.

Embodiment 9A is a surface treated inorganic dental filler of any one of embodiments 1A to 8A, wherein $R^9$ is a phenyl group.

Embodiment 10A is a surface treated inorganic dental filler of any one of embodiments 1A to 9A, wherein $R^{Si}$ is —$Si(OCH_3)_3$ or —$Si(OCH_2CH_3)_3$.

Embodiment 11A is a surface treated inorganic dental filler of any one of embodiments 1A to 10A, wherein the inorganic dental filler is selected from the group consisting of non-agglomerated particles, agglomerated particles, non-aggregated particles, aggregated particles, clusters, and combinations thereof.

Embodiment 12A is a surface treated inorganic dental filler of any one of embodiments 1A to 11A, wherein the inorganic dental filler is a non acid-reactive filler.

Embodiment 13A is a surface treated inorganic dental filler of any one of embodiments 1A to 12A, wherein the inorganic dental filler comprises nano-particles and/or clusters of nano-particles.

Embodiment 14A is a surface treated inorganic dental filler of any one of embodiments 1A to 13A, wherein the inorganic dental filler comprises metal oxide particles.

Embodiment 15A is a surface treated inorganic dental filler of any one of embodiments 1A to 14A, wherein the inorganic dental filler comprises particles selected from the group consisting of silica particles, zirconia particles, aluminosilicate glasses, doped aluminosilicate glasses, and combinations thereof.

Embodiment 16A is a surface treated inorganic dental filler of embodiment 15A, wherein the doped aluminosilicate glasses are selected from the group consisting of barium aluminosilicates, strontium aluminosilicates, lanthanum aluminosilicates, and combinations thereof.

Embodiment 17A is a surface treated inorganic dental filler of any one of embodiments 1A to 16A, wherein the inorganic dental filler comprises particles having an average particle size of 5 nanometers to 20 microns.

Embodiment 18A is a surface treated inorganic dental filler of any one of embodiments 1A to 17A, wherein the particles have at least 25% surface coverage of the particles with the at least one silane.

Embodiment 1B is a surface treated inorganic dental filler comprising a surface treated with at least one silane of the formula:

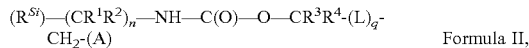

$(R^{Si})-(CR^1R^2)_n-NH-C(O)-O-CR^3R^4-(L)_q-CH_2-(A)$   Formula II, wherein: $R^{Si}$ is a silane-containing group of the formula $-Si(Y_p)(R^6)_{3-p}$, wherein Y is a hydrolysable group, $R^6$ is a monovalent alkyl or aryl group, and p is 1, 2, or 3; each $R^1$, $R^2$, and $R^3$ is independently H, an alkyl group, an aryl group, an alkaryl group, or an aralkyl group; $R^4$ is H, an alkyl group, an aryl group, an alkaryl group, or an aralkyl group, wherein the group may optionally be substituted with one or more catenary oxygen atoms, —O—C(O)— groups, and/or —C(O)—O— groups; n is 1 to 6; q is 0 or 1; L is a divalent alkylene group, a divalent arylene group, a divalent alkarlyene group, or a divalent aralkylene group, wherein the divalent group may optionally be substituted with one or more catenary oxygen atoms, —O—C(O)— groups, and/or —C(O)—O— groups; and A is a (meth)acryl group of the formula $X^1-C(O)-C(R^7)=CH_2$, wherein $X^1$ is —O, —S, or —$NR^7$, and each $R^7$ is independently H or a $C_1$-$C_4$ alkyl group; with the proviso that at least one of $R^1$, $R^2$, $R^3$, and $R^4$ is not H.

Embodiment 2B is a surface treated inorganic dental filler of embodiment 1B, wherein each $R^1$, $R^2$, and $R^3$ is independently H or $CH_3$.

Embodiment 3B is a surface treated inorganic dental filler of embodiments 1B or 2B, wherein $R^4$ is H, $CH_3$, or a group of the formula —$(CH_2)_m$-(A), wherein m is 1.

Embodiment 4B is a surface treated inorganic dental filler of any one of embodiments 1B to 3B, wherein q is 0.

Embodiment 5B is a surface treated inorganic dental filler of any one of embodiments 1B to 4B, wherein n is 1 to 3.

Embodiment 6B is a surface treated inorganic dental filler of any one of embodiments 1B to 5B, wherein A is —O—C(O)—CH=$CH_2$ or —O—C(O)—C($CH_3$)=$CH_2$.

Embodiment 7B is a surface treated inorganic dental filler of any one of embodiments 1B to 6B, wherein $R^{Si}$ is —$Si(OCH_3)_3$ or —$Si(OCH_2CH_3)_3$.

Embodiment 8B is a surface treated inorganic dental filler of any one of embodiments 1B to 7B, wherein L is

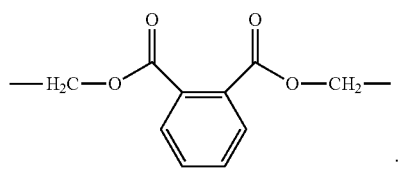 [SMILES: CCOC(=O)c1ccccc1C(=O)OCC]

Embodiment 9B is a surface treated inorganic dental filler of any one of embodiments 1B to 8B, wherein $R^4$ is —$CH_2$—O—C(O)-Ph.

Embodiment 10B is a surface treated inorganic dental filler of any one of embodiments 1B to 9B, wherein the inorganic dental filler is selected from the group consisting of non-agglomerated particles, agglomerated particles, non-aggregated particles, aggregated particles, clusters, and combinations thereof.

Embodiment 1B is a surface treated inorganic dental filler of any one of embodiments 1B to 10B, wherein the inorganic dental filler is a non acid-reactive filler.

Embodiment 12B is a surface treated inorganic dental filler of any one of embodiments 1B to 11B, wherein the inorganic dental filler comprises nano-particles and/or clusters of nano-particles.

Embodiment 13B is a surface treated inorganic dental filler of any one of embodiments 1B to 12B, wherein the inorganic dental filler comprises metal oxide particles.

Embodiment 14B is a surface treated inorganic dental filler of any one of embodiments 1B to 13B, wherein the inorganic dental filler comprises particles selected from the group consisting of silica particles, zirconia particles, aluminosilicate glasses, doped aluminosilicate glasses, and combinations thereof.

Embodiment 15B is a surface treated inorganic dental filler of embodiment 14B, wherein the doped aluminosilicate glasses are selected from the group consisting of barium aluminosilicates, strontium aluminosilicates, lanthanum aluminosilicates, and combinations thereof.

Embodiment 16B is a surface treated inorganic dental filler of any one of embodiments 1B to 15B, wherein the inorganic dental filler comprises particles having an average particle size of 5 nanometers to 20 microns.

Embodiment 17B is a surface treated inorganic dental filler of any one of embodiments 1B to 16B, wherein the particles have at least 25% surface coverage of the particles with the at least one silane.

Embodiment 1C is a hardenable dental composition comprising a surface treated inorganic filler according to any one of embodiments 1A to 17B.

Embodiment 2C is a hardenable dental composition of embodiment 1C, wherein the hardenable dental composition further comprises at least one polymerizable resin.

Embodiment 3C is a hardenable dental composition of embodiment 2C, wherein the at least one polymerizable resin is a free radically polymerizable resin.

Embodiment 4C is a hardenable dental composition of any one of embodiments 1C to 3C, wherein the hardenable dental composition further comprises additional surface treated and/or non-surface treated inorganic fillers.

Embodiment 5C is a hardenable dental composition of any one of embodiments 1C to 4C, wherein the hardenable dental composition further comprises an initiator system.

Embodiment 6C is a hardenable dental composition of embodiment 5C, wherein the initiator system is selected from the group consisting of photoinitiator systems, redox initiator systems, peroxide heat activated, and combinations thereof.

Embodiment 7C is a hardenable dental composition of any one of embodiments 1C to 6C, wherein the hardenable dental composition further comprises an additive selected from the group consisting of flavorants, fluoridating agents, buffering agents, numbing agents, remineralization agents, desensitization agents, colorants, indicator(s), viscosity modifiers, surfactants, stabilizers, preservative agents, and combinations thereof.

Embodiment 8C is a hardenable dental composition of any one of embodiments 1C to 7C, wherein the hardenable dental composition is a single part dental composition or a multi-part dental composition.

Embodiment 1D is a method of preparing a surface treated inorganic dental filler according to any one of embodiments 1A to 18A, the method comprising contacting an inorganic filler with at least one silane of the formula:

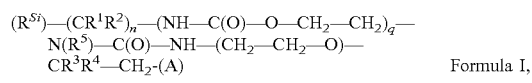

$(R^{Si})-(CR^1R^2)_n-(NH-C(O)-O-CH_2-CH_2)_q-N(R^5)-C(O)-NH-(CH_2-CH_2-O)-CR^3R^4-CH_2-(A)$   Formula I, wherein: $R^{Si}$ is a silane-containing group of the formula —$Si(Y_p)(R^6)_{3-p}$, wherein Y is a hydrolysable group, $R^6$ is a monovalent alkyl or aryl group, and p is 1, 2, or 3; each $R^1$, $R^2$, and $R^3$ is independently H, an alkyl group, an aryl group, an alkaryl group, or an aralkyl group; $R^4$ is H, an alkyl group, an aryl group, an alkaryl group, an aralkyl group, or a group of the formula —$(CH_2)_m$-(A), wherein m is 1 to 6; n is 1 to 6; q is 0 or 1; t is 0 or 1; A is a (meth)acryl group of the formula $X^1$—C(O)—C($R^7$)=$CH_2$, wherein $X^t$ is —O, —S, or —$NR^7$, and each $R^7$ is independently H or a $C_1$-$C_4$ alkyl group; and $R^5$ is H, an alkyl group, a cycloalkyl group, an aryl group, an alkaryl group, an aralkyl group, a group of the formula $(R^{Si})$—$(CR^1R^2)_n$—(NH—C(O)—O—$CH_2$—$CH_2)_q$—, a group of the formula $(R^{Si})$—$(CR^1R^2)_n$—NH—C(O)—N($R^8$)—$(CH_2)_m$—, a group of the formula —$(CH_2)_m$-(A), a group of the formula —$(CH_2)_m$—N($R^8$)—C(O)—NH—$(CH_2$—$CH_2$—O)$_t$—$CR^3R^4$—$CH_2$-(A), or a group of the formula —$(CH_2)_m$—N($R^8$)—C(O)—NH—$R^9$; wherein each m and n is independently 1 to 6, q is 0 or 1, t is 0 or 1, and each $R^1$, $R^2$, $R^3$, $R^4$, $R^{Si}$, and A are as defined above; $R^8$ is H or a group of the formula —$(CH_2)_m$—NH—C(O)—NH—$(CH_2$—$CH_2$—O)$_t$—$CR^3R^4$—$CH_2$-(A), a group of the formula —$(CH_2)_m$—NH—C(O)—NH—$(CR^1R^2)$—$(R^{Si})$, or a group of the formula —$(CH_2)_m$—NH—C(O)—NH—$R^9$, wherein each m and n is independently 1 to 6, t is 0 or 1, and each $R^1$, $R^2$, $R^3$, $R^4$, $R^{Si}$, and A are as defined above; and $R^9$ is an alkyl group, an aryl group, an alkaryl group, or an aralkyl group; with the proviso that at least one of $R^1$, $R^2$, $R^3$, $R^4$, and $R^5$ is not H.

Embodiment 2D is a method of embodiment 1D, wherein contacting comprises contacting the inorganic filler with the at least one silane in a liquid medium.

Embodiment 3D is a method of embodiment 2D wherein the liquid medium comprises at least one organic solvent.

Embodiment 4D is a method of embodiment 3D, wherein the at least one organic solvent is selected from the group consisting of alcohols, acetates, aromatics, ketones, and combinations thereof.

Embodiment 5D is a method of any one of embodiments 2D to 4D, wherein the liquid medium further comprises water.

Embodiment 6D is a method of any one of embodiments 2D to 5D, wherein the liquid medium further comprises at least one catalyst.

Embodiment 7D is a method of embodiment 6D, wherein the at least one catalyst is an acidic catalyst or a basic catalyst.

Embodiment 8D is a method of embodiment 7D, wherein the acidic catalyst is an organic acidic catalyst or an inorganic acidic catalyst.

Embodiment 9D is a method of embodiment 8D, wherein the organic acidic catalyst is selected from the group consisting of carboxylic acids, sulfonic acids, phosphonic acids, and combinations thereof.

Embodiment 10D is a method of embodiment 8D, wherein the inorganic acidic catalyst is selected from the group consisting of hydrochloric acid, nitric acid, sulfuric acid, phosphoric acid, antimonic acid, boric acid, and combinations thereof.

Embodiment 11D is a method of embodiment 7D, wherein the basic catalyst is an organic basic catalyst or an inorganic basic catalyst.

Embodiment 12D is a method of embodiment 11D, wherein the organic basic catalyst is an amine selected from the group consisting of primary amines, secondary amines, tertiary amines, and combinations thereof.

Embodiment 13D is a method of embodiment 11 D, wherein the inorganic basic catalyst is selected from the group consisting of sodium hydroxide, potassium hydroxide, calcium hydroxide, ammonium hydroxide, and combinations thereof.

Embodiment 14D is a method of any one of embodiments 2D to 13D, wherein contacting further comprises stirring or mixing the inorganic filler and the at least one silane in the liquid medium.

Embodiment 15D is a method of any one of embodiments 2D to 14D, wherein the method further comprises removing at least a portion of the liquid medium to provide a dry inorganic dental filler comprising a surface treated with the at least one silane.

Embodiment 16D is a method of embodiment 15D, wherein removing the liquid medium comprises a process selected from the group consisting of heating, reducing pressure, freeze drying, and combinations thereof.

Embodiment 1E is a method of preparing a surface treated inorganic dental filler according to any one of embodiments 1B to 17B, the method comprising contacting an inorganic filler with at least one silane of the formula:

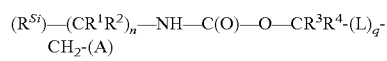

Formula II, wherein: $R^{Si}$ is a silane-containing group of the formula —Si($Y_p$)($R^6$)$_{3-p}$, wherein Y is a hydrolysable group, $R^6$ is a monovalent alkyl or aryl group, and p is 1, 2, or 3; each $R^1$, $R^2$, and $R^3$ is independently H, an alkyl group, an aryl group, an alkaryl group, or an aralkyl group; $R^4$ is H, an alkyl group, an aryl group, an alkaryl group, or an aralkyl group, wherein the group may optionally be substituted with one or more catenary oxygen atoms, —O—C(O)— groups, and/or —C(O)—O— groups; n is 1 to 6; q is 0 or 1; L is a divalent alkylene group, a divalent arylene group, a divalent alkarlyene group, or a divalent aralkylene group, wherein the divalent group may optionally be substituted with one or more catenary oxygen atoms, —O—C(O)— groups, and/or —C(O)—O— groups; and A is a (meth)acryl group of the formula $X^1$—C(O)—C($R^7$)=$CH_2$, wherein $X^1$ is —O, —S, or —$NR^7$, and each $R^7$ is independently H or a $C_1$-$C_4$ alkyl group; with the proviso that at least one of $R^1$, $R^2$, $R^3$, and $R^4$ is not H.

Embodiment 2E is a method of embodiment 1E, wherein contacting comprises contacting the inorganic filler with the at least one silane in a liquid medium.

Embodiment 3E is a method of embodiment 2E wherein the liquid medium comprises at least one organic solvent.

Embodiment 4E is a method of embodiment 3E, wherein the at least one organic solvent is selected from the group consisting of alcohols, acetates, aromatics, ketones, and combinations thereof.

Embodiment 5E is a method of any one of embodiments 2E to 4E, wherein the liquid medium further comprises water.

Embodiment 6E is a method of any one of embodiments 2E to 5E, wherein the liquid medium further comprises at least one catalyst.

Embodiment 7E is a method of embodiment 6E, wherein the at least one catalyst is an acidic catalyst or a basic catalyst.

Embodiment 8E is a method of embodiment 7E, wherein the acidic catalyst is an organic acidic catalyst or an inorganic acidic catalyst.

Embodiment 9E is a method of embodiment 8E, wherein the organic acidic catalyst is selected from the group consisting of carboxylic acids, sulfonic acids, phosphonic acids, and combinations thereof.

Embodiment 10E is a method of embodiment 8E, wherein the inorganic acidic catalyst is selected from the group consisting of hydrochloric acid, nitric acid, sulfuric acid, phosphoric acid, antimonic acid, boric acid, and combinations thereof.

Embodiment 11E is a method of embodiment 7E, wherein the basic catalyst is an organic basic catalyst or an inorganic basic catalyst.

Embodiment 12E is a method of embodiment 11E, wherein the organic basic catalyst is an amine selected from the group consisting of primary amines, secondary amines, tertiary amines, and combinations thereof.

Embodiment 13E is a method of embodiment 11E, wherein the inorganic basic catalyst is selected from the group consisting of sodium hydroxide, potassium hydroxide, calcium hydroxide, ammonium hydroxide, and combinations thereof.

Embodiment 14E is a method of any one of embodiments 2E to 13E, wherein contacting further comprises stirring or mixing the inorganic filler and the at least one silane in the liquid medium.

Embodiment 15E is a method of any one of embodiments 2E to 14E, wherein the method further comprises removing at least a portion of the liquid medium to provide a dry inorganic dental filler comprising a surface treated with the at least one silane.

Embodiment 16E is a method of embodiment 15E, wherein removing the liquid medium comprises a process selected from the group consisting of heating, reducing pressure, freeze drying, and combinations thereof.

Embodiment 1F is a hardened dental composition comprising a surface treated inorganic filler according to any one of embodiments 1A to 17B.

Embodiment 2F is a hardened dental composition of embodiment 1F, wherein the hardened dental composition further comprises additional surface treated and/or non-surface treated inorganic fillers.

Embodiment 3F is a hardened dental composition of embodiment 1F or 2F, wherein the hardened dental composition has a CUSP value with an absolute value of no more than 8 microns.

Embodiment 4F is a hardened dental composition of any one of embodiments 1F to 3F, wherein the hardened dental composition has a DTS of at least 60 MPa.

Embodiment 1G is a method of preparing a hardened dental composition, the method comprising: providing a hardenable dental composition according to any one of embodiments 1C to 8C; and providing conditions effective to harden the hardenable dental composition.

Embodiment 2G is a method of embodiment 1G, wherein conditions effective to harden the dental composition comprise a process selected from the group consisting of heating, irradiating, combining parts of a multi-part dental composition, vacuum starvation, and combinations thereof.

Objects and advantages of this disclosure are further illustrated by the following non-limiting examples, but the particular materials and amounts thereof recited in these examples, as well as other conditions and details, should not be construed to unduly limit this disclosure.

EXAMPLES

The following examples are given to illustrate, but not limit, the scope of this invention. As used herein, all parts and percentages are by weight and all water was deionized, unless otherwise specified. Unless otherwise specified, materials can be obtained from Sigma-Aldrich Corp. (St. Louis, Mo.).

Description of Abbreviations and Acronyms

Monomers of the Polymerizable Resin

"AFM-1" is an addition-fragmentation monomer which can be prepared as described in U.S. Pat. No. 9,056,043 (Joly et al.) at column 46, line 58 through column 47, line 27 ("Preparation of AFM-1");

"BisGMA" refers to 2,2-bis[4-(2-hydroxy-3-methacryloyloxypropoxy)phenyl]propane (also referred to as bisphenol A diglycidyl ether methacrylate), available from Sigma-Aldrich Corp. (St. Louis, Mo.);

"Procrylat K" refers to 2,2-Bis-4-(3-hydroxy-propoxyphenyl)propane dimethacrylate (CAS 27689-2-9);

"DDDMA" refers to 1,12-dodecanediol dimethacrylate, available under the trade designation "SR-262" from Sartomer Co., Inc. (Exton, Pa.);

"ERGP-IEM" refers to 2-propenoic acid, 2-methyl-, 1,1'-[1,3-phenylenebis[oxy-2,1-ethanediyloxy[1-(phenoxymethyl)-2,1-ethanediyl]oxycarbonylimino-2,1-ethanediyl]] ester, which can be prepared as described at column 77, lines 33-40 of U.S. Pat. No. 8,710,113 (Eckert et al.) ("Synthesis of ERGP-IEM");

"TEGDMA" refers to triethyleneglycol dimethacrylate, available from Sartomer Co., Inc. (Exton, Pa.);

"UDMA" refers to diurethane dimethacrylate, available under the trade designation "ROHAMERE 6661-0" from Rohm America LLC (Piscataway, N.J.); also available from Dajac Laboratories (Trevose, Pa.);

"BisEMA-6" refers to ethoxylated (6) Bisphenol A dimethacrylate;

"PEG600 DM" refers to polyethylene glycol dimethacrylate (600);

"S/T Silica/Zirconia Clusters" refers to silane-treated silica-zirconia nanocluster filler, prepared generally as described in U.S. Pat. No. 6,730,156 (Windisch et al.) at column 25, lines 50-63 (Preparatory Example A) and at column 25, line 64 through column 26, line 40 (Preparatory Example B) with minor modifications, including performing the silanization in 1-methoxy-2-propanol (rather than water) adjusted to a pH of approximately 8.8 with aqueous $NH_4OH$ (rather than to a pH of 3-3.3 with trifluoroacetic acid), and obtaining the nanocluster filler by gap drying (rather than spray drying).

Nanoparticles:

"S/T 20 nm Silica" refers to silane-treated silica nanoparticle filler having a nominal particle size of approximately 20 nanometers, prepared substantially as described in U.S. Pat. No. 6,572,693 at column 21, lines 63-67 ("Nanosized particle filler, Type #2");

"S/T Nanozirconia" refers to silane-treated zirconia filler, which was prepared from the zirconia sol substantially as described in U.S. Pat. No. 8,647,510 (Kolb et al.) at column 36 line 61 to column 37, line 16 (Example 11A-IER). The zirconia sol was added to an equivalent weight of 1-methoxy-2-propanol containing GF-31 (1.1 mmol of GF-31 per gram of nanozirconia to be surface treated). The mixture was heated to approximately 85° C. for 3 hours with stirring. The mixture was cooled to 35° C., adjusted to a pH of approximately 9.5 with aqueous $NH_4OH$, and the mixture reheated to approximately 85° C. for 4 hours with stirring. The resultant material was washed with an excess of water, and t S/T Nanozirconia was isolated as a dry powder via gap drying to remove solvents. As used herein, "S/T Nanozirconia" also refers to silane-treated zirconia filler which is solvent exchanged into the resins (and pastes) without isolating the S/T Nanozirconia in dry powder form (e.g., by addition of the S/T Nanozirconia sol to a methacrylate-containing resin, followed by concentration at reduced pressure and/or heating to remove volatiles associated with the sol, as further detailed in the examples herein).

Coupling Agent/Surface Treatment

"GF-31" refers to 3-methacryloxypropyltrimethoxysilane, available from Wacker Chemie AG (Munich, Germany).

Other precursors were available, for example, from Gelest, Aldrich, and TCI America.

Other Components:

"YbF$_3$" refers to ytterbium fluoride, approximately 100-105 nm particle size, refractive index 1.52 available from Sukgyung AT Co. Ltd., (Korea);

"BHT" refers to butylated hydroxytoluene (2,6-di-tert-butyl-4-methylphenol), available from Sigma-Aldrich Corp. (St. Louis, Mo.);

"BZT" refers to 2-(2'-hydroxy-5'-methacryloxyethylphenyl)-2H-benzotriazole, available from Ciba, Inc. (Tarrytown, N.Y.) as "TINUVIN R 796", also available from Sigma-Aldrich Corp. (St. Louis, Mo.);

"CPQ" refers to camphorquinone;

"DPIHFP" or "DPIPF6" refers to diphenyliodonium hexafluorophosphate, available from Johnson Matthey, Alfa Aesar Division (Ward Hill, Mass.);

"EDMAB" refers to ethyl 4-(dimethylamino)benzoate, available from Sigma-Aldrich Corp. (St. Louis, Mo.).

Silane Preparatory Example—Group A

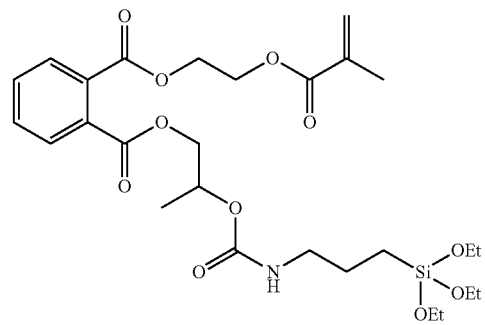 [SMILES: C=C(C)C(=O)OCCOC(=O)c1ccccc1C(=O)OCC(C)OC(=O)NCCC[Si](OCC)(OCC)OCC]

Silane 2 Preparatory Example—Propyl Cyclohexyl IEMA Urea Silane 7-cyclohexyl-3,3-dimethoxy-8-oxo-2-oxa-7,9-diaza-3-silaundecan-11-yl methacrylate

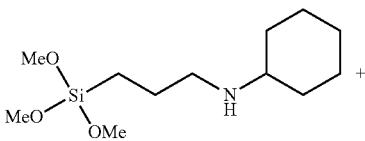

TABLE 1

Materials for Silane Preparatory Examples - Group A

| Material Type | CAS Number | Description (Acronym) |
|---|---|---|
| Isocyanate | 30674-80-7 | 2-isocyanatoethyl methacrylate (IEMA) from Showa Denko, Japan |
| Isocyanate | 13641-96-8 | 2-isocyanatoethyl acrylate (IEA) from Showa Denko, Japan |
| Isocyanate-silane | 24801-88-5 | 3-(Triethoxysilyl)propyl isocyanate |
| Aminosilane | 3068-78-8 | (N-Cyclohexylaminopropyl) trimethoxysilane from Gelest |
| Aminosilane | 3068-76-6 | (N-Phenylaminopropyl) trimethoxysilane from Gelest |
| Aminosilane | 3473-76-5 | (N-Phenylaminomethyl) triethoxysilane from Gelest |
| Aminosilane | 227085-51-0 | (3-(N-Ethylamino)isobutyl) trimethoxysilane from Gelest |
| Aminosilane | 31024-56-3 | n-Butylaminopropyl Trimethoxysilane from Gelest |
| Aminosilane | 3069-30-5 | 4-Aminobutyltriethoxysilane from Gelest |
| Aminosilane | 157923-74-5 | 4-Amino-3,3-Dimethylbutyl Trimethoxysilane from Gelest |
| Aminosilane | 3069-25-8 | N-Methylaminopropyl trimethoxysilane from Gelest |
| Aminosilane | 1760-24-3 | N-(2-aaminoethyl)-3-aminopropyl trimethoxysilane from Gelest |
| Aminosilane | 51895-58-0 | N-(6-aminohexyl)aminopropyl trimethoxysilane from Gelest |
| Aminosilane | 121772-92-7 | N-(2-aminoethyl)-11-aminoundecyl trimethoxysilane from Gelest |
| GMA | 106-91-2 | Glycidyl methacrylate (GMA) from TCI America |
| Methacrylate carbonate | 13818-44-5 | ((2-oxo-1,3-dioxolan-4-yl)methyl 2-methylprop-2-enoate) |
| t-butylaminoethyl methacrylate | 3775-90-4 | t-Butylaminoethyl methacrylate from Sigma Aldrich, Milwaukee, WI, USA |

Silane 1 Preparatory Example—Phthalate Methacrylate Urethane Silane 14.9884 grams of 3-isocyanatopropyltriethoxysilane was mixed with 20.4350 g 2-hydroxypropyl 2-(methacryloyloxy)-ethyl phthalate. To this mixture, with stirring, was added 1 drop of dibutyl tin dilaurate. The sample was allowed to react, with an exotherm noted.

-continued

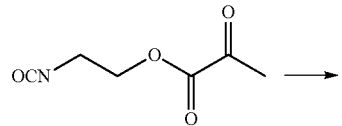

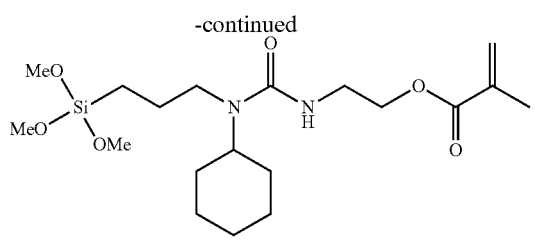

21.398 grams aminosilane was combined with 11.6 mL IEMA with stirring. Reaction exothermed to 92° C., then subsided to room temperature after 1 hour. Material was obtained as a clear, colorless to slightly yellow, low viscosity liquid in quantitative yield.

Silane 3 Preparatory Example—Propyl Phenyl IEMA Urea Silane 3,3-dimethoxy-8-oxo-7-phenyl-2-oxa-7,9-diaza-3-silaundecan-11-yl methacrylate

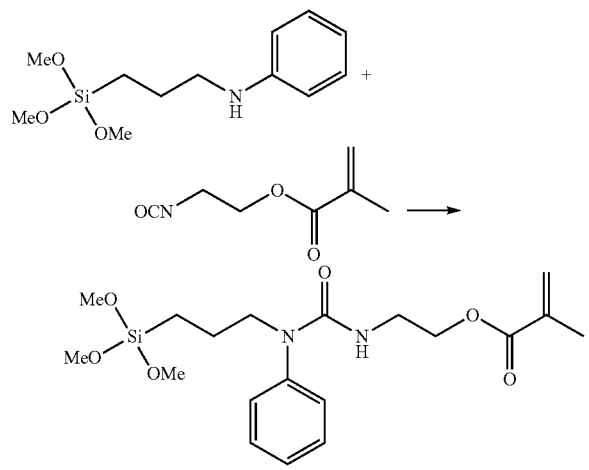

100.013 grams aminosilane was combined with 55.5 mL IEMA with stirring, at a rate sufficient to keep the reaction temperature under 50° C., about 10 mL at a time. Material was obtained as a clear, colorless to slightly yellow, low viscosity liquid in quantitative yield.

Silane 4 Preparatory Example—Methyl Phenyl IEMA Urea Silane.3,3-dimethoxy-6-oxo-5-phenyl-2-oxa-5,7-diaza-3-silanonan-9-yl methacrylate

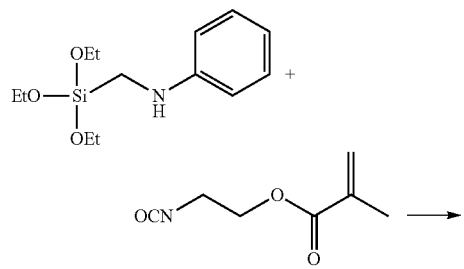

100.013 grams aminosilane was combined with 55.5 mL IEMA with stirring, at a rate sufficient to keep the reaction temperature under 50° C., about 10 mL at a time. Material was obtained as a clear, colorless to slightly yellow, low viscosity liquid in quantitative yield.

Silane 5 Preparatory Example—Isobutyl Ethyl IEMA Urea Silane 7-ethyl-3,3-dimethoxy-5-methyl-8-oxo-2-oxa-7,9-diaza-3-silaundecan-11-yl methacrylate

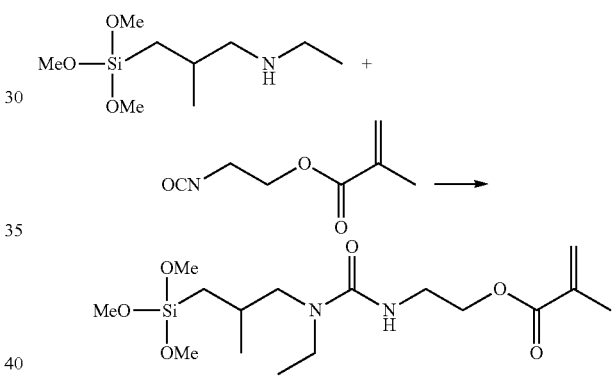

11.012 grams aminosilane was combined with 7 mL IEMA with stirring, at a rate sufficient to keep the reaction temperature under 55° C., about 1 mL IEMA at a time. Material was obtained as a clear, light yellow, thick liquid in quantitative yield.

Silane 6 Preparatory Example—Propyl Butyl IEMA Urea Silane 7-butyl-3,3-dimethoxy-8-oxo-2-oxa-7,9-diaza-3-silaundecan-11-yl methacrylate

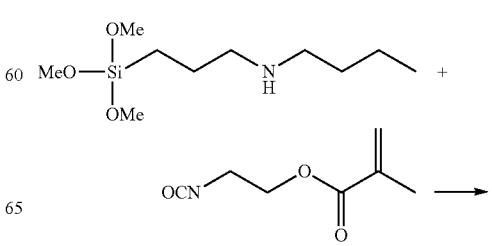

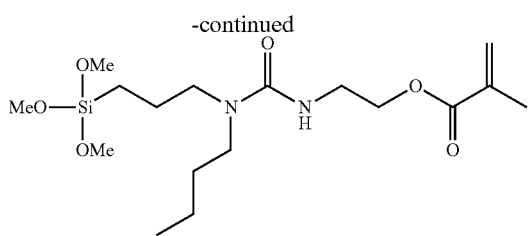

10.016 grams aminosilane was combined with 6 mL IEMA with stirring, at a rate sufficient to keep the reaction temperature under 55° C., about 1 mL IEMA at a time. Material was obtained as a clear, colorless to slightly yellow, low viscosity liquid in quantitative yield.

Silane 7 Preparatory Comparative Example—Butyl IEMA Urea Silane 4,4-diethoxy-10-oxo-3-oxa-9,11-diaza-4-silatridecan-13-yl methacrylate

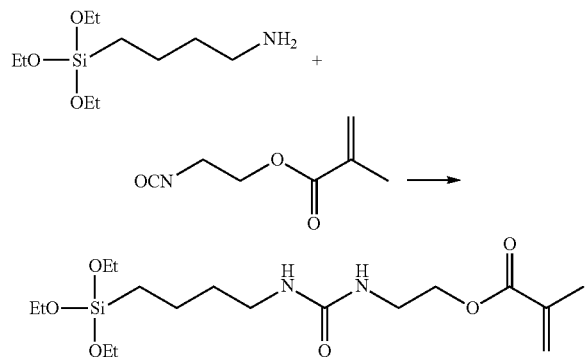

10.006 grams aminosilane was combined with 6 mL IEMA with stirring, at a rate sufficient to keep the reaction temperature under 55° C., about 1 mL IEMA at a time. Material was obtained as a clear, colorless to slightly yellow, low viscosity liquid in quantitative yield.

Silane 8 Preparatory Example—Dimethylbutyl IEMA Urea Silane 3,3-dimethoxy-6,6-dimethyl-9-oxo-2-oxa-8,10-diaza-3-siladodecan-12-yl methacrylate

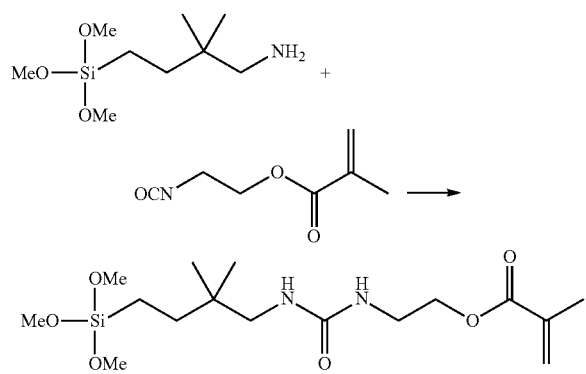

11.002 grams aminosilane was combined with 7 mL IEMA with stirring, at a rate sufficient to keep the reaction temperature under 60° C., about 1 mL IEMA at a time. Material was obtained as a clear, colorless to slightly yellow, viscous liquid in quantitative yield.

Silane 9 Preparatory Example—Propyl Methyl IEMA Urea Silane 3,3-dimethoxy-7-methyl-8-oxo-2-oxa-7,9-diaza-3-silaundecan-11-yl methacrylate

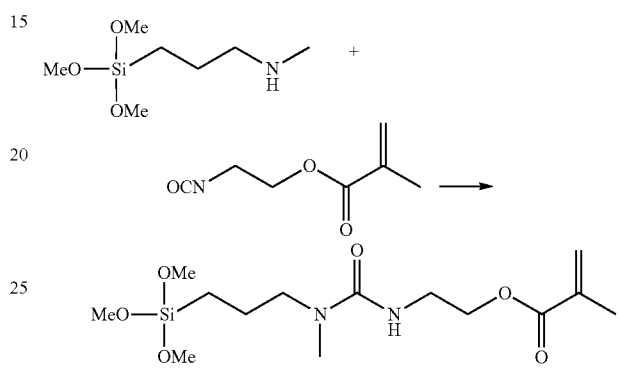

11.008 grams aminosilane was combined with 8 mL IEMA with stirring, at a rate sufficient to keep the reaction temperature under 60° C., about 1 mL IEMA at a time. Material was obtained as a clear, colorless to slightly yellow, low viscosity liquid in quantitative yield.

Silane 10 Preparatory Example—Propyl Phenyl IEA Urea Silane 3,3-dimethoxy-8-oxo-7-phenyl-2-oxa-7,9-diaza-3-silaundecan-11-yl acrylate

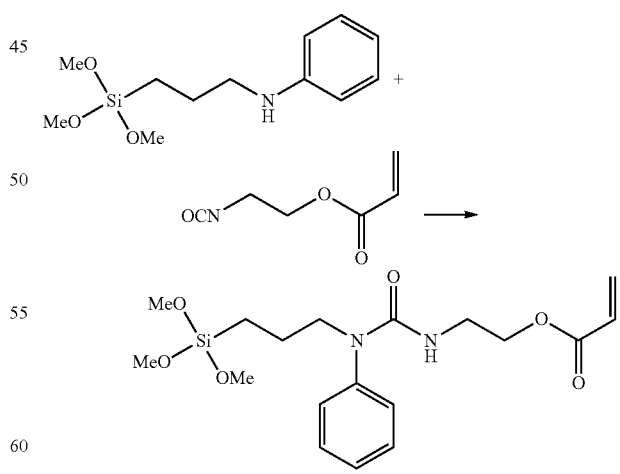

25.003 grams aminosilane was combined with 12.2 mL IEA with stirring, at a rate sufficient to keep the reaction temperature under 45° C., about 1 mL IEA at a time. Material was obtained as a clear, colorless to slightly yellow, low viscosity liquid in quantitative yield.

Silane 11 Preparatory Example—Dimethylbutyl IEA Urea Silane 3,3-dimethoxy-6,6-dimethyl-9-oxo-2-oxa-8,10-diaza-3-siladodecan-12-yl acrylate

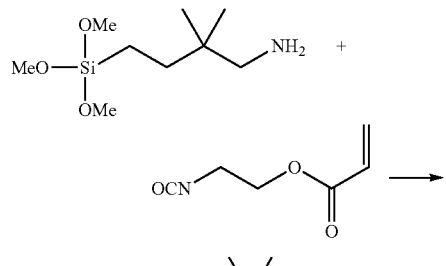

11.003 grams aminosilane was combined with 6.2 mL IEA with stirring, at a rate sufficient to keep the reaction temperature under 75° C., about 1 mL IEA at a time. Material was obtained as a clear, colorless, viscous liquid in quantitative yield.

Silane 12 Preparatory Example—Isobutyl Ethyl IEA Urea Silane 7-ethyl-3,3-dimethoxy-5-methyl-8-oxo-2-oxa-7,9-diaza-3-silaundecan-11-yl acrylate

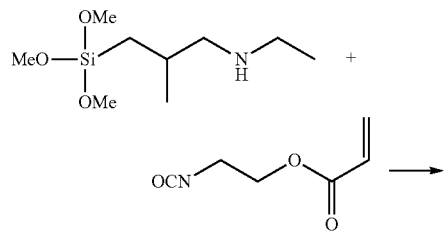

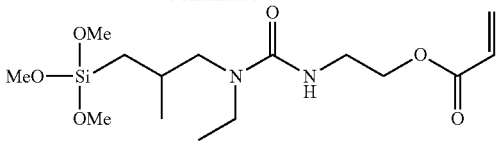

11.010 grams aminosilane was combined with 6.2 mL IEA with stirring, at a rate sufficient to keep the reaction temperature under 65° C., about 1 mL IEA at a time. Material was obtained as a clear, colorless, low viscosity liquid in quantitative yield.

Silane 13 Preparatory Example—Propyl Ethyl Bis-IEMA Urea Silane 4,9-dioxo-5-(3-(trimethoxysilyl)propyl)-3,5,8,10-tetraazadodecane-1,12-diyl bis(2-methylacrylate)

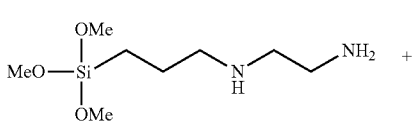

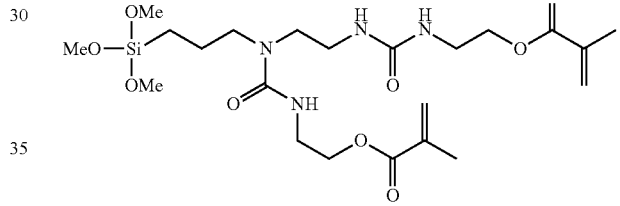

10.25 grams aminosilane was combined with 13 mL IEMA with stirring, at a rate sufficient to keep the reaction temperature under 55° C., about 1 mL IEMA at a time. Material was obtained as a clear, colorless to slightly yellow, viscous liquid in quantitative yield.

Silane 14 Preparatory Example—Propyl Hexyl Bis-IEMA Urea Silane 4,13-dioxo-5-(3-(trimethoxysilyl)propyl)-3,5,12,14-tetraazahexadecane-1,16-diyl bis(2-methylacrylate)

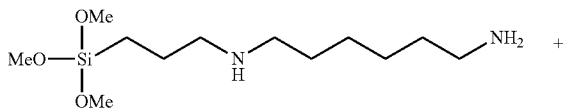

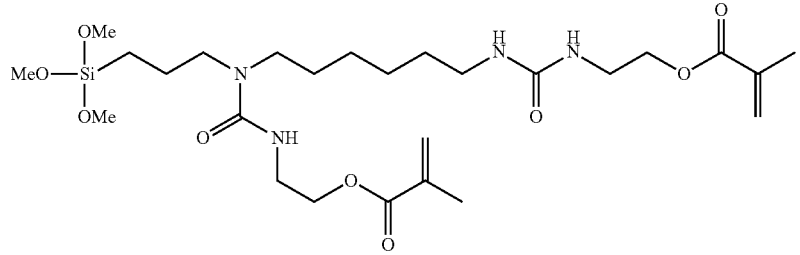

10.60 grams aminosilane was combined with 12 mL IEMA with stirring, at a rate sufficient to keep the reaction temperature under 55° C., about 1 mL IEMA at a time. Material was obtained as a clear, colorless to slightly yellow, viscous liquid in quantitative yield.

Silane 15 Preparatory Comparative Example—Propyl t-Butyl Urea Silane.10-(tert-butyl)-4,4-diethoxy-9-oxo-3-oxa-8,10-diaza-4-siladodecan-12-yl methacrylate

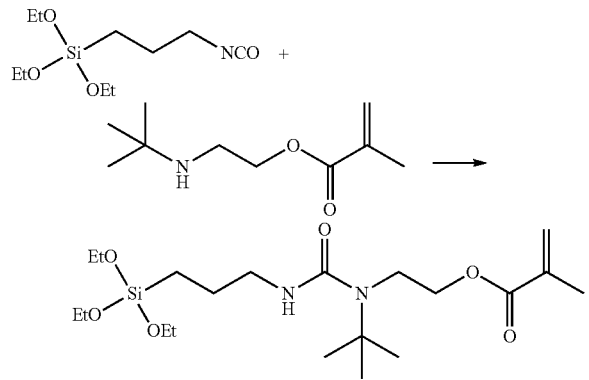

10 grams silane-isocyanate was combined with 7.49 grams amine with stirring. Reaction exothermed to 45° C. Material was obtained as a clear, colorless to slightly yellow, low viscosity liquid in quantitative yield.

Silane 16 Preparatory Example—Benzoate glycidyl methacrylate urethane propyl triethoxysilane

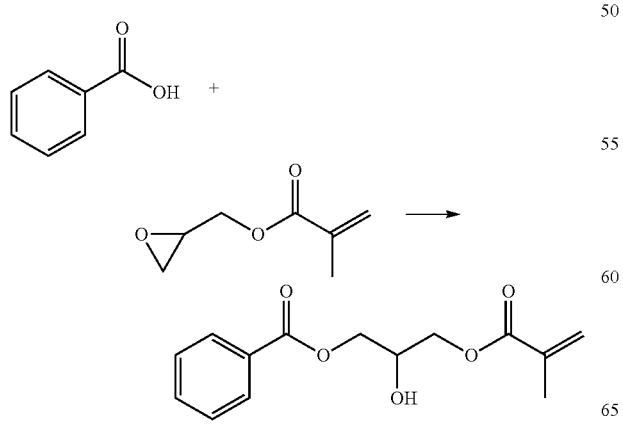

Benzoic acid (31.89 grams, 261 mmol, GFS Chemicals Inc., Powell, Ohio, USA) was mixed with glycidyl methacrylate (37.12 grams, 261 mmol, TCI America, Portland, Oreg., USA) in a 250 3-neck round bottom flask equipped with a mechanical stirrer and a condenser. The condenser was open to the surrounding air. Triphenyl antimony (0.3 grams, 0.8 mmol, Fluka) was added. The heterogeneous mixture was heated in an oil bath (oil temperature=100-105° C.). The mixture became clear after a few minutes heating time at 100° C.). After 2 hours of continuous heating and stirring, trhiphenyphosphine (0.1 grams, 0.4 mmol, Alfa Aesar, Tewksbury, Mass., 01876, USA) was added and heating/stirring were continued overnight. Next day, the heat was turned off and after cooling to room temperature, a liquid product was obtained in an quantitative yield. Product structure was confirmed by 1H NMR. This product was reacted with a mixture of: 10 grams of benzoic acid glycidyl methacrylate ester, 9.37 grams of 3-isocyanatopropyltriethoxysilane and 1 drop of dibutyl tin dilaurate, with stirring, the resulting mixture exothermed, converting to Silane 16 with the following structure.

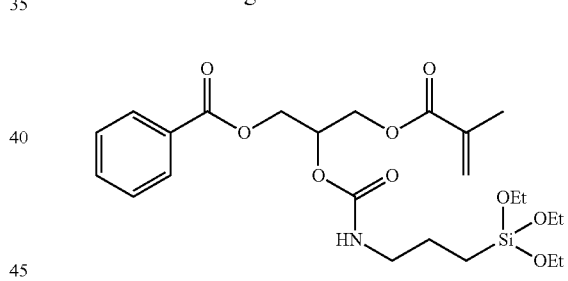

Silane 17 Preparatory Comparative Example

GENISOSIL GF 31 available from Wacker Chemie AG.

3-methacryloxypropyltrimethoxysilane

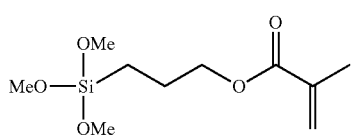 [SMILES: C=C(C)C(=O)OCCC[Si](OC)(OC)OC]

Silane 18 Preparatory Comparative Example—Undecyl Ethyl Bis-IEMA Urea Silane 4,9-dioxo-5-(11-(trimethoxysilyl)undecyl)-3,5,8,10-tetraazadodecane-1,12-diyl bis(2-methylacrylate)

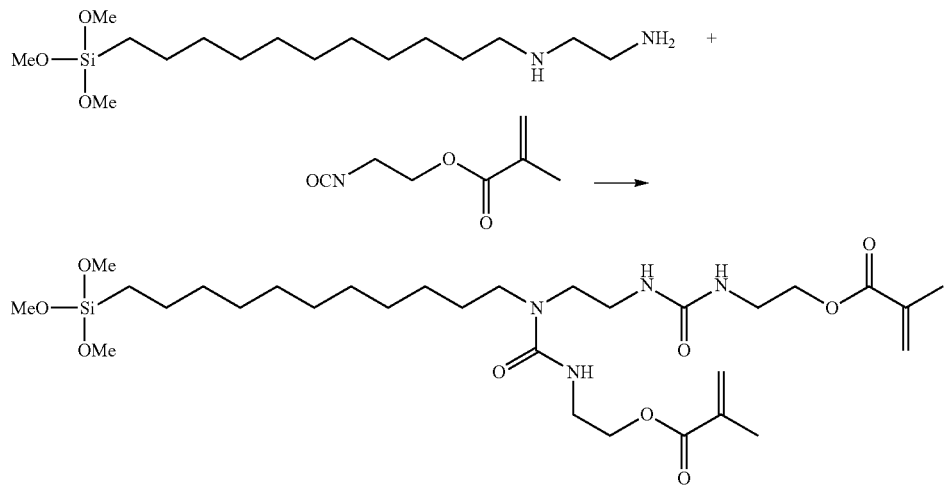

5.118 grams aminosilane was combined with 4.3 mL IEMA with stirring, at a rate sufficient to keep the reaction temperature under 70° C., about 1 mL IEMA at a time. Material was obtained as a clear, colorless to slightly yellow, viscous liquid in quantitative yield.

Silane 19 Preparatory Comparative Example—Propyl Phenyl GCMA Urethane Silane 11-hydroxy-3,3-dimethoxy-8-oxo-7-phenyl-2,9-dioxa-7-aza-3-siladodecan-12-yl methacrylate

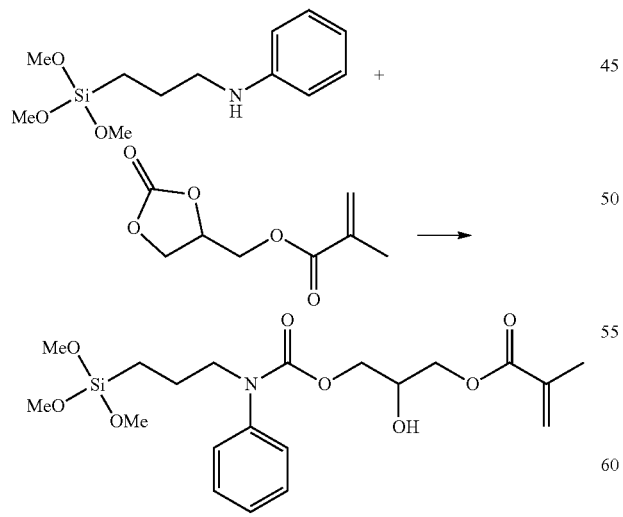

8.23 grams aminosilane was combined with 6.00 grams cyclic carbonate (CAS 13818-44-5) with stirring. Reaction was stirred at room temperature overnight to give clear, colorless, low viscosity liquid in quantitative yield.

Silane 20 Preparatory Comparative Example—Propyl Phenyl GMA Silane 2-hydroxy-3-(phenyl(3-(trimethoxysilyl)propyl)amino)propyl methacrylate

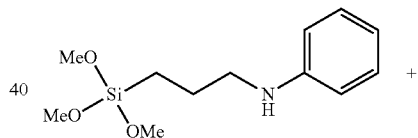

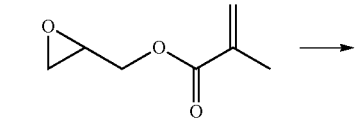

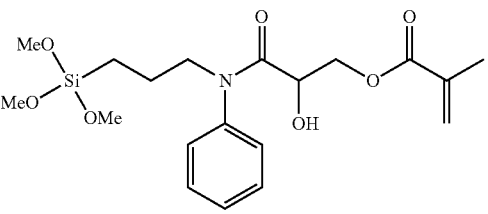

11.53 grams aminosilane was combined with 6.0 mL glycidyl methacrylate and a crumb of DMAP with stirring. Reaction was stirred at room temperature overnight to give clear, colorless, low viscosity liquid in quantitative yield.

Silane 21 Preparatory Comparative Example—HEMA-Urethane Triethoxysilane

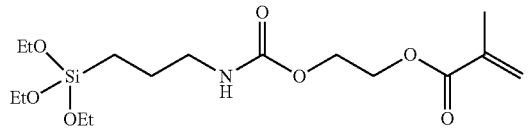 [SMILES: C=C(C)C(=O)OCCOC(=O)NCCC[Si](OCC)(OCC)OCC]

Equimolar amounts of 3-isocyanatopropyltriethoxysilane and 2-hydroxyethyl methacrylate were mixed together with stirring. To this was added 1-2 drops of dibutyl tin dilaurate catalyst. The reaction was allowed to proceed with a noticeable exotherm.

Silane 22 Preparatory Comparative Example—KBM-5803 from from Shin-Etsu Silicones of America, Inc. Akron, Ohio, USA)

8-methacryloxyoctyltrimethoxysilane

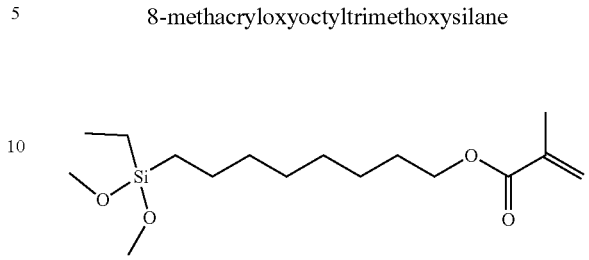

Silane Preparatory Examples—Group B

TABLE 2

Materials for Silane Preparatory Examples - Group B

| Material Type | CAS Number | Description (Acronym) Source |
|---|---|---|
| (Meth)acrylated material with isocyanate functionality | 886577-76-0 | 1,1-bis(acryloyloxymethyl) ethyl isocyanate (BEI) from CBC America Corp., Commack, NY, USA |
| (Meth)acrylated material with isocyanate functionality | 13641-96-8 | 2-Isocyanatoethyl acrylate (IEA) from CBC America Corp. |
| (Meth)acrylated material with isocyanate functionality | 30674-80-7 | Isocyanatoethyl methacrylate (IEM) from CBC America Corp. |
| Silane material with isocyanate functionality | 15396-00-6 | 3-Isocyanatopropyltrimethoxysilane (Geniosil GF-40) from Wacker Silicones, Adrian, MI, USA |
| Silane material with isocyanate functionality | 24801-88-5 | 3-Isocyanatopropyltriethoxysilane (Silquest A-Link 25) from Momentive Performance Materials, Garrett, IN, USA |
| Catalyst | 77-58-7 | Dibutyltin dilaurate (DBTDL) from Sigma Aldrich, Milwaukee, WI, USA |
| Solvent | 78-93-3 | Methyl ethyl ketone (MEK) from EMD Chemicals, Inc., Billerica, MA, USA |
| Solvent | 141-78-6 | Ethyl acetate (EtOAc) from EMD Chemicals, Inc. |
| Aminosilane | 26495-91-0 | N-cyclohexyl-triethoxysilylmethylamine (Geniosil XL 926) from Wacker Silicones |
| Aminosilane | 13822-56-5 | (3-Aminopropyl)trimethoxysilane (Dynasylan AMMO) from Evonik Piscataway, NJ, USA |
| Aminosilane | 919-30-2 | (3-Aminopropyl)triethoxysilane (Dynasylan AMEO ) from Evonik |
| Aminosilane | 82985-35-1 | bis(3-trimethoxysilylpropyl)amine (Dynasylan 1124) from Evonik |
| Aminosilane | 13497-18-2 | bis(3-triethoxysilylpropyl)amine (Dynasylan 1122) from Evonik |
| Aminosilane | 31024-56-3 | N-(n-butyl)-3-aminopropyltrimethoxysilane (Dynasylan 1189) from Evonik |
| Aminosilane | 3069-25-8 | N-methyl-3-aminopropyltrimethoxysilane from SynQuest Labs, Alachua, FL, USA |
| Aminosilane | 3068-76-6 | 3-(phenylamino)propyltrimethoxysilane from Sigma Aldrich |
| Aminosilane | 3068-78-8 | 3-(cyclohexylamino) propyltrimethoxysilane |
| Aminosilane | 3473-76-5 | N-(phenylamino)methyltriethoxysilane |

TABLE 3

Materials for Silane Preparatory Examples - Group B

| Material Type | CAS Number | Description (Acronym) Source |
|---|---|---|
| Aminosilane | — | 3-Amino-2,2-dimethyl-propyltrimethoxysilane |
| Aminosilane | 227085-51-0 | N-ethyl-3-trimethoxysilyl-methylpropamine (A-Link 15) from Momentive Performance Materials, |
| Aminosilane | 1760-24-3 | 3-(2-Aminoethylamino) propyl trimethoxysilane from Sigma-Aldrich |
| Aminosilane | 35141-30-1 | 3-trimethoxysilylpropyldiethylenetriamine from Oakwood Chemical, Estill, SC, USA |
| Aminosilane | — | 3-(2-Aminohexylamino) propyl trimethoxysilane from Sigma-Aldrich |
| Amino-acrylate | 3775-90-4 | 2-(tert-Butylamino)ethyl methacrylate from Sigma-Aldrich |
| Methacryloxy carbonate | — | Methacryloxymethyl-ethylene carbonate |
| Epoxy-methacrylate | 106-91-2 | Glycidyl methacrylate available from Sigma-Aldrich |

TABLE 3-continued

Materials for Silane Preparatory Examples - Group B

| Material Type | CAS Number | Description (Acronym) Source |
|---|---|---|
| Amino alcohol | 141-43-5 | Ethanolamine from Sigma-Aldrich |
| Amino alcohol | 109-83-1 | N-methylethanolamine from Sigma-Aldrich |
| Radical stabilizer | 128-37-0 | 2,6-Di-t-butyl-4-methylphenol (BHT) from Sigma-Aldrich |
| Radical stabilizer | 2226-96-2 | 4-Hydroxy-2,2,6,6-tetramethylpiperidine 1-oxyl, (4-hydroxy TEMPO) from Sigma-Aldrich |
| Cyclic carbonate | 96-49-1 | Ethylene carbonate (EC) from Sigma Aldrich |
| Acrylate-methacrylate | 69040-48-8 | 2-methacryloxyethyl acrylate available from JieJie Group Co., Ltd. (Shanghai, China) |
| Phenyl isocyanate | 103-71-9 | Available from Sigma Aldrich CAS |

Silane 23 Preparatory Example

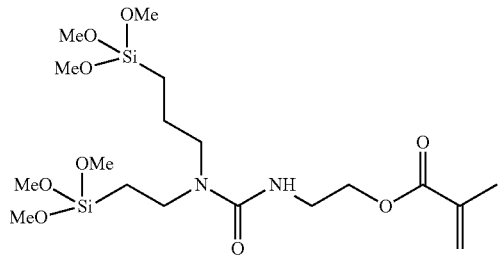 [SMILES: C=C(C)C(=O)OCCNC(=O)N(CCC[Si](OC)(OC)OC)CC[Si](OC)(OC)OC]

A 250 mL round-bottom flask with a stirbar was charged with 40 grams (0.117 mol, 341.55 MW) bis(3-trimethoxysilylpropylamine (Dynasylan 1124) and placed in an ice bath. Via a pressure equalizing addition funnel, 18.17 grams (0.117 mol) isocyanatoethyl methacrylate (IEM) was added over about 25 minutes. The ice bath was removed and stirring continued for another hour and 15 minutes. At that point, a sample was taken for Fourier Transform Infrared (FTIR) spectroscopic analysis, the sample showed no isocyanate peak (–NCO) at 2265 cm$^{-1}$. The product, a clear oil, was then isolated.

Silane 24 Preparatory Example

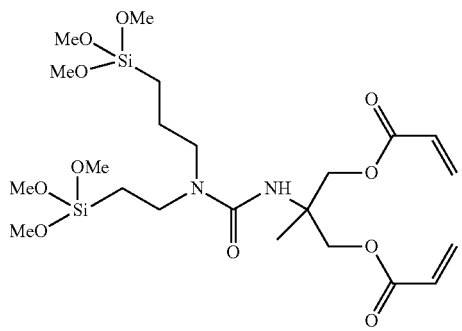 [SMILES: C=CC(=O)OCC(C)(COC(=O)C=C)NC(=O)N(CCC[Si](OC)(OC)OC)CC[Si](OC)(OC)OC]

A 250 mL three necked round-bottom flask equipped with an overhead stirrer was charged with 12.36 grams (0.0517 mol, 239.23 MW) 1,1-bis(acryloyloxymethyl) ethyl isocyanate (BEI), and 176 microliters of a 10% solution of DBTDL in MEK (500 ppm based on the total weight of reactants). The flask was placed in a 35° C. oil bath, and 17.64 grams (0.517 mol, 341.55 MW) bis-(3-trimethoxysilylpropyl) amine (Dynasylan 1124) was added to the reaction via dropping funnel over 1 hour. About 10 minutes after the amine addition was complete, a sample was taken for FTIR, the sample showed no isocyanate peak at 2265 cm$^{-1}$. The product, a clear oil, was then isolated.

Silane 25 Preparatory Example

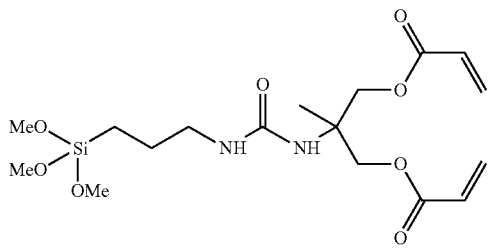 [SMILES: C=CC(=O)OCC(C)(COC(=O)C=C)NC(=O)NCCC[Si](OC)(OC)OC]

An experiment was run similar to Silane 24 Preparatory Example, except that 12.85 grams (0.072 mol, 179.29 MW) aminopropyltrimethoxysilane (Dynasylan AMMO) was reacted with 17.15 grams (0.072 mol) 1,1-bis(acryloyloxymethyl) ethyl isocyanate (BEI), and 176 microliters of a 10% solution of DBTDL in MEK (500 ppm DBTDL) over about 45 minutes to provide the product as an oil.

Silane 26 Preparatory Example

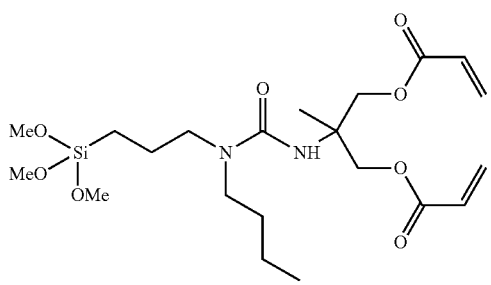 [SMILES: C=CC(=O)OCC(C)(COC(=O)C=C)NC(=O)N(CCCC)CCC[Si](OC)(OC)OC]

An experiment was run similar to Silane 24 Preparatory Example, except that 9.92 grams (0.042 mol, 235.4 MW) N-butyl-3-aminopropyltrimethoxysilane (Dynasylan 1189) was added to 10.08 grams (0.042 mol) 1,1-bis(acryloyloxymethyl) ethyl isocyanate (BEI), with no DBTDL over about 1 hour, then reacted overnight to provide the product as an oil.

Silane 27 Preparatory Example

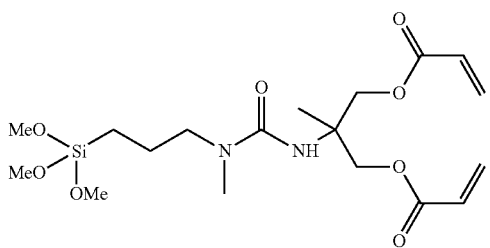 [SMILES: C=CC(=O)OCC(C)(COC(=O)C=C)NC(=O)N(C)CCC[Si](OC)(OC)OC]

An experiment was run similar to Silane 24 Preparatory Example, except that 8.94 grams (0.046 mol, 193.32 MW) N-methyl-3-aminopropyltrimethoxysilane was added to 11.06 grams (0.046 mol) 1,1-bis(acryloyloxymethyl) ethyl isocyanate (BEI), with no DBTDL over about 30 minutes. At about 4 hours, the reaction was monitored by FTIR showing an –NCO peak, and 0.3 grams of N-methyl-3-aminopropyltrimethoxysilane was added with a drop of DBTDL. After 1 hour, the reaction was monitored by FTIR showing a diminished –NCO peak. At this point, 0.1 gram N-methyl-3-aminopropyltrimethoxysilane was added, and after 1 hour, the reaction was complete by FTIR to provide the product as an oil.

Silane 28 Preparatory Example

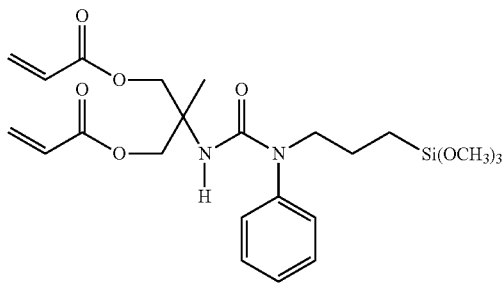

An experiment was run similar to Silane 24 Preparatory Example, except that 10.33 grams (0.0404 mol, 255.39 MW) 3-(phenylamino)propyltrimethoxysilane was added to 10.33 grams (0.0404 mol) 1,1-bis(acryloyloxymethyl) ethyl isocyanate (BEI), with 1 drop DBTDL over about 30 minutes, then reacted overnight to provide the product as an oil.

Silane 29 Preparatory Example

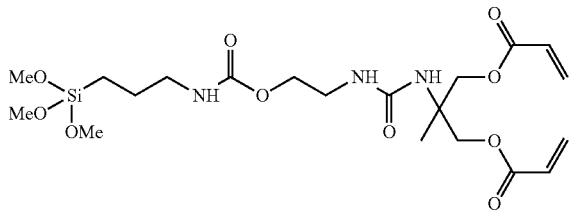 [SMILES: C=CC(=O)OCC(C)(COC(=O)C=C)NC(=O)NCCOC(=O)NCCC[Si](OC)(OC)OC]

A pressure equalizing addition funnel was charged with 23.66 grams (0.0988 mol) BEI. A second pressure equalizing funnel was charged with 6.04 grams (0.0988 mol) ethanolamine and adjusted to the same volume as the BEI with ethyl acetate. The funnels were placed on a 100 mL three-necked flask equipped with stir bar, and the flask was placed in an ice bath under dry air. The ethanol amine and BEI were added to the flask at the same volume rate over 45 minutes. At about 2 hours, the funnels were rinsed with a few mL of ethyl acetate, and about 0.025 gram of DBTDL was added. The reaction was placed in a room temperature water bath, and 20.30 grams (0.0988 mol) 3-isocyanatopropyltrimethoxysilane (Geniosil GF-40) was added via a pressure equalizing funnel over about 20 minutes. After addition, the funnel was rinsed with a few mL of ethyl acetate. After about 6 additional hours, the reaction was complete by FTIR. The reaction was then concentrated at up to 55° C. and about 3 mm of pressure to provide the product as a thick oil.

Silane 30 Preparatory Example

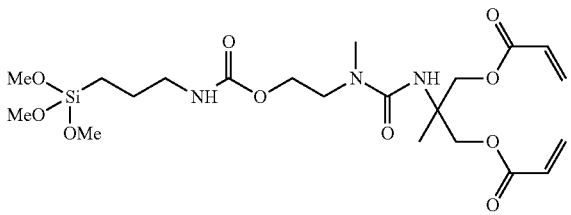 [SMILES: C=CC(=O)OCC(C)(COC(=O)C=C)NC(=O)N(C)CCOC(=O)NCCC[Si](OC)(OC)OC]

In a manner similar to that for Silane 29 Preparatory Example, 23.02 grams (0.0962 mol) BEI, 7.23 grams (0.0962 mol) N-methyl-ethanolamine, followed by 19.75 grams (0.0962 mol) 3-isocyanatopropyltrimethoxysilane, and 0.025 grams DBTDL were processed to provide the desired product, Silane 30.

Silane 31 Preparatory Example

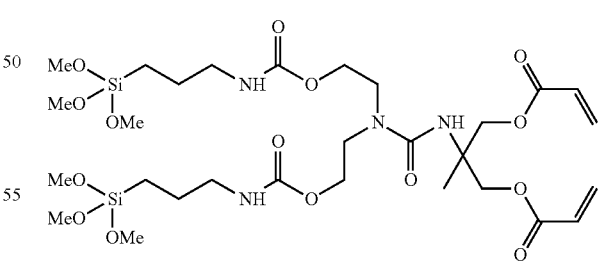

In a manner similar to that for Silane 29 Preparatory Example, 15.84 grams (0.0662 mol) BEI, 6.96 grams (0.0662 mol) diethanolamine, followed by 27.19 grams (0.1324 mol) 3-isocyanatopropyltrimethoxysilane and 0.025 grams DBTDL were processed to provide the desired product, Silane 31. Before removing the ethyl acetate, about 0.010 grams BHT and 0.002 grams 4-hydroxy TEMPO were added to the reaction to provide Silane 31.

Silane 32 Preparatory Comparative Example

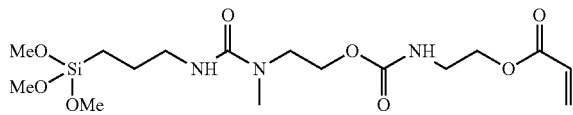 [SMILES: C=CC(=O)OCCNC(=O)OCCN(C)C(=O)NCCC[Si](OC)(OC)OC]

In a manner similar to that for Silane 29 Preparatory Example, 21.91 grams (0.1068 mol) 3-isocyanatopropyltrimethoxysilane, 8.02 grams (0.1068 mol) N-methylethanolamine, followed by 15.07 grams (0.1068 mol) IEA and 0.025 grams DBTDL were processed to provide the desired product, Silane 32.

Silane 33 Preparatory Comparative Example

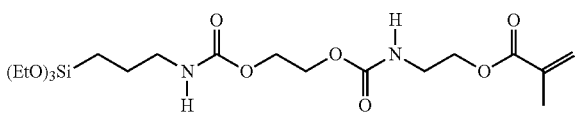

A 250 mL round bottom flask was charged with 19.89 grams (0.2259 mol) of ethylene carbonate and placed in a 55° C. oil bath. Using a pressure equalizing dropping funnel, 50.0 grams (0.2259 mol) of aminopropyltriethoxysilane (Dynasylan AMEO) was added over the course of 10 minutes. Heating was continued for 2 hours to provide a $(EtO)_3Si—(CH_2)_3—NH—C(O)—O—CH_2CH—OH$.

A fresh 250 mL round bottom flask was charged 33.78 grams (0.2177 mol) of isocyanatoethyl methacrylate (IEM) and about 1000 ppm DBTDL and placed in a 55° C. oil bath. To the flask was added 67.37 grams (0.2177 mol) $(EtO)_3Si—(CH_2)_3—NH—C(O)—O—CH_2CH—OH$ over the course of 30 minutes. Heating was continued for 1.5 hours of additional reaction time. A sample was then taken for FTIR spectroscopic analysis, the sample showed no isocyanate peak at 2265 cm$^{-1}$.

Silane 34 Preparatory Comparative Example

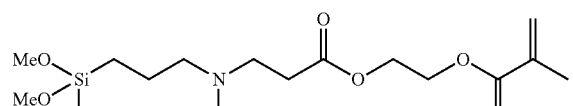

A 100 ml round-bottom equipped with stirbar was charged with 27.62 grams (0.15 mol, 184.15 MW) 2-methacryloxyethyl acrylate and 27.38 grams (0.15 mol, 193.32 MW) N-methyl-3-aminopropyltrimethoxysilane and heated to 55° C. under dry air for 2 hours to provide the product as an oil.

Silane 35 Preparatory Example

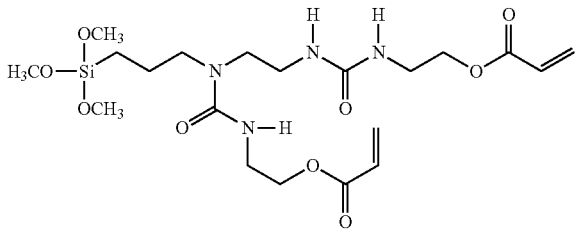 [SMILES: C=CC(=O)OCCNC(=O)NCCN(CCC[Si](OC)(OC)OC)C(=O)NCCOC(=O)C=C]

A 250 mL three necked round-bottom flask equipped with an overhead stirrer was charged with 30.76 grams (0.218 eq, 141.12 EW) IEA, and 30.76 grams EtOAc. The flask was placed in an ice bath under dry air. A pressure equalizing funnel was charged with 24.24 grams (0.218 eq, 111.18 EW) 3-(2-Aminoethylamino)-propyltrimethoxysilane. The funnel was placed on the flask and the 3-(2-Aminoethylamino) propyltrimethoxysilane was added dropwise over 1 hour 15 minutes, keeping the temperature below 10° C. The funnel was then rinsed with approximately 2 grams of EtOAc. At 2 hours 15 minutes, an FTIR was taken on an aliquot of the reaction, and no –NCO peak was found. To the reaction was added about 0.28 grams BHT and about 0.12 grams 4-hydroxy TEMPO. The reaction was then distilled under vacuum to remove EtOAc at up to 60° C. and 3.8 mm pressure to provide the product.

Silane 36 Preparatory Example

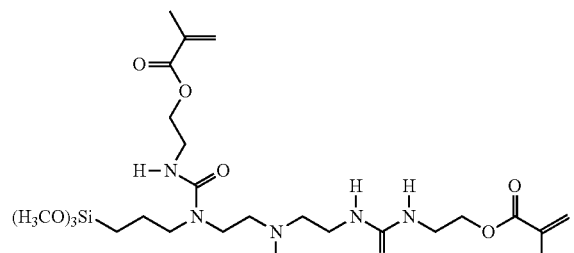

In a manner similar to that for Silane 35 Preparatory Example, 35.03 grams (0.2258 eq, 155.15 EW) IEM in 35.03 grams EtOAc was reacted with 21.37 grams (0.2416 eq, 1.07 times calculated equal stoichiometry, 88.48 EW) 3-trimethoxysilylpropyldiethylenetriamine in 21.37 grams EtOAc, and concentrated to provide a thick oil.

Silane 37 Preparatory Example

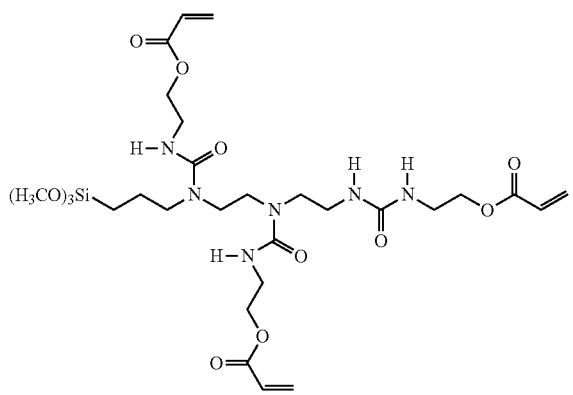

In a manner similar to that for Silane 35 Preparatory Example, 33.81 grams (0.2396 eq, 141.12 EW) IEA in 33.71 grams EtOAc was reacted with 22.68 grams (0.2563 eq., 1.07 times calculated equal stoichiometry, 88.48 EW) 3-trimethoxysilylpropyldiethylenetriamine in 22.68 grams EtOAc, and concentrated to provide a thick oil.

Silane 38 Preparatory Example

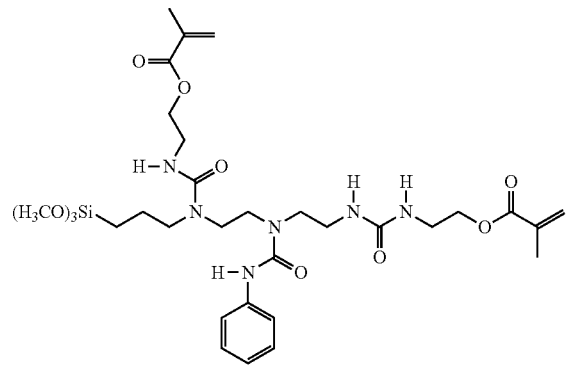

The Preparatory Example is a mixture of materials, and one of the constituents is displayed above. By the method of preparation, there will exist some materials whose nitrogen atom has been functionalized with at least one IEM and at least one Phenyl isocyanate.

A 250 mL three necked round-bottom flask equipped with an overhead stirrer was charged with 23.89 grams (0.2699 eq., 1.07 times calculated equal stoichiometry, 88.48 EW) 3-trimethoxysilylpropyldiethylenetriamine and 23.89 grams EtOAc. The flask was placed in an isopropanol-water dry ice bath under dry air and cooled to −50° C. A pressure equalizing funnel was charged with 26.10 grams (0.1682 eq, 155.15 EW) IEM in 26.10 grams EtOAc which was added to the reaction over about 55 minutes at a temperature no higher than −46° C. A pressure equalizing funnel was charged with 10.02 grams (0.0841 eq., 119.12 EW) phenyl isocyanate, which was added to the reaction over about 25 minutes at a temperature no higher than −37° C. The reaction was sampled at this temperature for FTIR and found to have a very small NCO peak. To the reaction was added about 0.25 grams of BHT and 0.012 grams of 4-hydroxy TEMPO, which was concentrated under vacuum to remove EtOAc at up to 60° C. and 3.8 mm pressure to provide the product as a thick oil.

Preparatory Example: Resin A

A 1200 gram batch of Resin A was prepared by mixing the following:

TABLE 4

| Resin A Composition | | |
|---|---|---|
| Description | Quantity (grams) | Percent (%) |
| ERGP-IEM | 8260.0 | 68.83 |
| UDMA | 2252.0 | 18.77 |
| DDDMA | 1039.0 | 8.66 |
| AFM 1 Monomer | 180.0 | 1.50 |
| EDMAB | 132.0 | 1.10 |
| CPQ | 33.6 | 0.28 |
| BZT | 60.0 | 0.50 |
| BHT | 6.0 | 0.05 |
| Iodonium | 36.0 | 0.30 |

Preparatory Example: Cluster Filler Preparation

Each of the clusters was reacted with a silane preparatory example by the following method. An amount of 100 grams of untreated silica/zirconia cluster was weighed into a mixture of 100 grams of ethyl acetate and 10.5 grams of each of the various silane preparatory examples. Once this mixture was stirring, 2 grams of 30 wt % NH4OH aqueous solution was added to the slurry, and the mixture allowed to react overnight to surface modify the cluster filler. The cluster fillers were subsequently dried in a solvent oven at 85-90° C. for 1.5 hours. Cluster fillers will be designated by the silane preparatory example that was put onto them. Cluster Filler 1=cluster treated with silane preparatory example 1; Cluster Filler 2=cluster treated with silane preparatory example 2, etc.

Final Paste Examples also included additional stock fillers including: 3-methacryloxy propyltrimethoxysilane treated 20 nm silica, and 3-methacryloxy propyltrimethoxysilane treated nanozirconia.

Example Paste Preparations

Note, all pastes were prepared via. speed mixer (Flak Tek), unless otherwise noted.

Example Paste Control

The Example Paste CONTROL was made by mixing the following ingredients.

TABLE 5

| Paste CONTROL Composition. | |
|---|---|
| 65.956% | Silane treated Cluster Filler 17, treated with Silane Preparatory Comparative Example 17 |
| 2.974% | 20 nm silane treated silica |
| 1.601% | Silane treated nanozirconia |
| 5.719% | YbF$_3$ (100 nm) |
| 23.75% | Resin A |

Example Pastes 1-16, 18-34

Example Pastes 1-16, 18-34 were made by mixing ingredients as in the Example Paste CONTROL except changing the cluster filler (that was treated with the respective silane preparatory example) in each instance. Accordingly, Example Paste 1 contained the same ingredients, in the same amounts, as Example Paste CONTROL (above) except that Cluster Filler 1, treated with Silane Preparatory Example 1 was used instead of Preparative Comparative Example Silane 17 treated Cluster Filler 17. Likewise, Example Paste 2 contained the same ingredients, in the same amounts, as Example Paste CONTROL (above) except that Cluster Filler 2, treated with Silane Preparatory Example 2 was used instead of Silane 17 treated Cluster Filler 17. Note, there is no Example Paste 17 because Silane Preparatory Example 17 is used in Example Paste CONTROL.

Physical Properties Testing:

Stress Test Method (Cusp Deflection Test)

To measure stress development during the curing process, a slot was machined into a rectangular 15×8×8 mm aluminum block. The slot was 8 mm long, 4 mm deep, and 2 mm across, and was located 2 mm from an edge, thus forming a 2 mm wide aluminum cusp adjacent to a 2 mm wide cavity containing dental compositions being tested. A linear variable displacement transducer (Model GT 1000, used with an E309 analog amplifier, both from RDP Electronics, United Kingdom) was positioned to measure the displacement of the cusp tip as the dental composition photocured at room temperature. Prior to testing, the slot in the aluminum block was sandblasted using Rocatec Plus Special Surface Coating Blasting Material (3M Oral Care), treated with RelyX Ceramic Primer (3M Oral Care, St. Paul, Minn., USA), and finally treated with a commercially available dental adhesive (SCOTCHBOND Universal Adhesive, available from 3M Oral Care). A substantially similar machined aluminum block and testing apparatus are depicted FIGS. 1 and 2 of U.S. Pat. No. 9,056,043 (Joly et al.).

The slot was fully packed with each of the Example Pastes. The material was irradiated for 1 minute with a dental curing light (ELIPAR S-10, 3M Oral Care) positioned almost in contact (<1 mm) with the test material in the slot, then the displacement of the cusp in microns was recorded 9 minutes after the light was extinguished. Numbers closer to 0 indicate lower deflection, and thus lower stresses.

Diametral Tensile Strength

Diametral tensile strength was measured per the following procedure. The uncured composite sample was injected into a glass that was about 30 mm long with a 4-mm inside diameter. It was filled about ½ full and capped with silicone rubber plugs. The tube was compressed axially at approximately 3 kg/cm$^2$ pressure for 5 minutes. While still under pressure, the sample was then light cured for 60 seconds by exposure to a dental curing light with a radiant exitance of greater than 1000 mW/cm$^2$. The tube was rotated as it cured to ensure equal exposure. A Buehler IsoMet 4000 (Illinois Tool Works, Lake Bluff, Ill., USA) saw was then used to section disks about 2 mm thick from the tube. The resulting disks were stored in distilled water at 37° C. for about 24 hours prior to testing Measurements were carried out using an appropriate materials test frame (e.g., Instron 5966, Instron Corp., Canton, Mass.) with a 10 kilonewton load cell at a crosshead speed of 1 mm per minute. Diametral tensile strength was calculate as describe in Craig's Restorative Dental Materials, (Ronals L. Sakaguchi and John M. Powers. "Testing of Dental Materials and Biomechanics." Craig's Restorative Dental Materials, thirteenth ed., Elsevier, 2012, p. 86). Results were reported in MPa. Higher numbers (MPa) indicate greater strengths.

Test Results

Physical properties test results are shown in Tables 6 and 7 for Example Pastes 1-16, 18-34, and Example Paste CONTROL, in descending Cusp Deflection value.

TABLE 6

| Example Paste | Cluster Filler | Silane Preparatory Example | Precursor MW (g/mol) | MW (g/mol) | DTS (MPa) | Cusp Deflection (μm) |
|---|---|---|---|---|---|---|
| CONTROL (Comparative) | 17 | Silane 17 (Comp. Ex.) | 248.35 | N/A | 78.83 | −10.89 |
| 22 (Comparative) | 22 | Silane 22 (Comp. Ex.) | — | — | 79.71 | −9.91 |
| 34 | 34 | Silane 34 (Comp. Ex.) | 377.51 | — | 63.02 | −9.00 |
| 21 (Comparative) | 21 | Silane 21 (Comp. Ex.) | 377.51 | 247.37 | 71.26 | −9.00 |
| 7 (Comparative) | 7 | Silane 7 (Comp. Ex.) | 390.55 | 235.4 | 74.96 | −8.77 |
| 33 (Comparative) | 33 | Silane 33 (Comp. Ex.) | 464.59 | 309.43 | 63.43 | −8.17 |
| 16 | 16 | Silane 16 | 511.64 | — | 73.28 | −7.86 |
| 9 | 9 | Silane 9 | 348.47 | 193.32 | 74.72 | −7.54 |
| 6 | 6 | Silane 6 | 390.55 | 235.4 | 74.84 | −7.28 |
| 23 | 23 | Silane 23 | 496.7 | 341.55 | 79.03 | −7.05 |
| 24 | 24 | Silane 24 | 580.78 | 341.55 | 81.5 | −6.77 |
| 1 | 1 | Silane 1 | 583.71 | — | 73.74 | −6.67 |
| 5 | 5 | Silane 5 | 376.53 | 221.37 | 80.49 | −6.67 |
| 27 | 27 | Silane 27 | 432.55 | 193.32 | 72.77 | −6.55 |
| 18 (Comparative) | 18 | Silane 18 (Comp. Ex.) | 644.88 | 334.58 | 63.49 | −6.35 |
| 8 | 8 | Silane 8 | 376.53 | 221.37 | 76.49 | −6.28 |
| 30 | 30 | Silane 30 | 519.62 | 205.29 | 69.64 | −6.24 |

TABLE 7

| Example Paste | Cluster Filler | Silane Preparatory Example | MW (g/mol) | Precursor MW (g/mol) | DTS (MPa) | Cusp Deflection (μm) |
|---|---|---|---|---|---|---|
| CONTROL (Comparative) | 17 | Silane 17 (Comp. Ex.) | 248.35 | N/A | 78.83 | −10.89 |
| 26 | 26 | Silane 26 | 474.63 | 235.4 | 70.87 | −6.12 |
| 31 | 31 | Silane 31 | 754.93 | 205.29 | 73.18 | −6 |
| 20 (Comparative) | 20 | Silane 20 (Comp. Ex.) | — | — | 50.66 | −5.84 |
| 15 (Comparative) | 15 | Silane 15 (Comp. Ex.) | 432.63 | 247.37 | 51.23 | −5.82 |
| 25 | 25 | Silane 25 | 418.52 | 179.29 | 82.13 | −5.59 |
| 28 | 28 | Silane 28 | — | — | 70.53 | −5.51 |
| 11 | 11 | Silane 11 | 362.5 | 221.37 | 78.16 | −5.42 |
| 4 | 4 | Silane 4 | 424.57 | 269.42 | 71.89 | −5.24 |
| 2 | 2 | Silane 2 | 416.59 | 261.44 | 70.91 | −5.15 |
| 3 | 3 | Silane 3 | 410.54 | 255.39 | 76.46 | −5.08 |
| 29 | 29 | Silane 29 | 505.6 | 205.29 | 75.82 | −5.07 |
| 32 (Comparative) | 32 | Silane 32 (Comp. Ex.) | 421.52 | 205.29 | 62.81 | −5.00 |
| 19 (Comparative) | 19 | Silane 19 (Comp. Ex.) | — | — | 57.78 | −4.92 |
| 10 | 10 | Silane 10 | 396.52 | 255.39 | 74.9 | −4.67 |
| 12 | 12 | Silane 12 | 362.5 | 221.37 | 75.98 | −4.61 |
| 13 | 13 | Silane 13 | 532.67 | 222.36 | 79.75 | −4.03 |
| 14 | 14 | Silane 14 | 588.77 | 278.47 | 75.35 | −3.77 |

All cited references, patents, or patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A surface-treated inorganic dental filler comprising:
an inorganic filler comprising particles having an average particle size of 5 nanometers to 20 microns, the particles having a surface modified with at least one silane represented by Formula I:

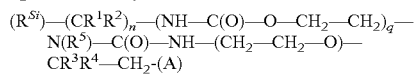

$(R^{Si})$—$(CR^1R^2)_n$—(NH—C(O)—O—$CH_2$—$CH_2)_q$— $N(R^5)$—C(O)—NH—($CH_2$—$CH_2$—O)$_t$— $CR^3R^4$—$CH_2$-(A)    Formula I, wherein:
each $R^{Si}$ is independently a silane-containing group of the formula —Si($Y_p$)($R^6$)$_{3-p}$;
Y is a hydrolysable group;
each $R^1$, $R^2$, and $R^3$ is independently selected from H, an alkyl group, an aryl group, an alkaryl group, and an aralkyl group;
each $R^4$ is independently selected from H, an alkyl group, an aryl group, an alkaryl group, an aralkyl group, and a group of the formula —($CH_2$)$_m$-(A);
each A is independently a (meth)acryl group of the formula $X^1$—C(O)—C($R^7$)=$CH_2$;
$X^1$ is —O, —S, or —$NR^7$
$R^5$ is H, an alkyl group, a cycloalkyl group, an aryl group, an alkaryl group, an aralkyl group, a group of the formula $(R^{Si})$—$(CR^1R^2)_n$—(NH—C(O)—O—$CH_2$—$CH_2)_q$—, a group of the formula $(R^{Si})$—$(CR^1R^2)_n$—NH—C(O)—N(R')—($CH_2$)$_m$—, a group of the formula —($CH_2$)$_m$-(A), a group of the formula —($CH_2$)$_m$—N(R')—C(O)—NH—($CH_2$—$CH_2$—O)$_t$—$CR^3R^4$—$CH_2$-(A), or a group of the formula —($CH_2$)$_m$—N($R^8$)—C(O)—NH—$R^9$;

$R^6$ is a monovalent alkyl or aryl group;
each $R^7$ is independently H or a $C_1$-$C_4$ alkyl group;
$R^8$ is H or a group of the formula —($CH_2$)$_m$—NH—C(O)—NH—($CH_2$—$CH_2$—O)$_t$—$CR^3R^4$—$CH_2$-(A), a group of the formula —($CH_2$)$_m$—NH—C(O)—NH—$(CR^1R^2)_n$—$(R^{Si})$, or a group of the formula —($CH_2$)$_m$—NH—C(O)—NH—$R^9$,
each $R^9$ is independently selected from an alkyl group, an aryl group, an alkaryl group, and an aralkyl group;
each m is independently an integer selected from 1 to 6;
each n is independently an integer selected from 1 to 6;
p is an integer selected from 1, 2, and 3
each q is independently 0 or 1; and
each t is independently 0 or 1,
with the proviso that at least one of $R^1$, $R^2$, $R^3$, $R^4$, and $R^5$, as shown in Formula I, is not H.

2. The surface-treated inorganic dental filler of claim 1, wherein the at least one silane is of the formula:

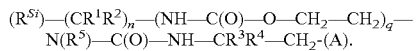

$(R^{Si})$—$(CR^1R^2)_n$—(NH—C(O)—O—$CH_2$—$CH_2)_q$— $N(R^5)$—C(O)—NH—$CR^3R^4$—$CH_2$-(A).

3. A surface-treated inorganic dental filler comprising:
an inorganic filler comprising particles having a surface modified with at least one silane represented by Formula II:

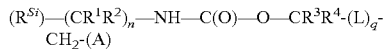

$(R^{Si})$—$(CR^1R^2)_n$—NH—C(O)—O—$CR^3R^4$-(L)$_q$-$CH_2$-(A)    Formula II, wherein:
$R^{Si}$ is a silane-containing group of the formula —Si($Y_p$)($R^6$)$_{3-p}$;
Y is a hydrolysable group,
$R^1$, $R^2$, and $R^3$ are independently selected from H, an alkyl group, an aryl group, an alkaryl group, and an aralkyl group;
$R^4$ is H, an alkyl group, an aryl group, an alkaryl group, an aralkyl group, or —$CH_2$—O—C(O)-Ph,
wherein the alkyl group, aryl group, alkaryl group, or aralkyl group may optionally be substituted with one or more of a catenary oxygen atom, —O—C(O)— groups, and —C(O)—O— groups;

L is a divalent alkylene group, a divalent arylene group, a divalent alkarylene group, a divalent aralkylene group, or

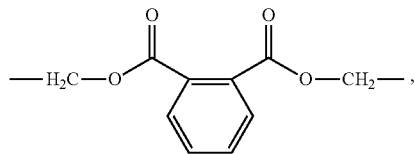 [SMILES: CCOC(=O)c1ccccc1C(=O)OCC]

wherein the divalent alkylene group, divalent arylene group, divalent alkarylene group, or divalent aralkylene group may optionally be substituted with one or more of a catenary oxygen atom, —O—C(O)— groups, and —C(O)—O— groups; and A is a (meth)acryl group of the formula $X^1$—C(O)—C($R^7$)=$CH_2$;

$X^1$ is —O—, —S—, or —$NR^7$;

$R^6$ is a monovalent alkyl or aryl group;

each $R^7$ is independently H or a $C_1$-$C_4$ alkyl group;

n is 1 to 6;

q is 0 or 1; and p is 1, 2, or 3, with the proviso that at least one of $R^1$, $R^2$, $R^3$, and $R^4$, as shown in Formula II, is not H.

4. The surface-treated inorganic dental filler of claim 1, wherein each $R^1$, $R^2$, and $R^3$ is independently H or $CH_3$.

5. The surface-treated inorganic dental filler of claim 1, wherein $R^4$ is H, $CH_3$, or a group of the formula —$(CH_2)_m$-(A), wherein m is 1.

6. The surface-treated inorganic dental filler of claim 1, the at least one silane is of the formula:

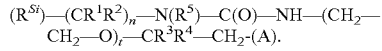

7. The surface-treated inorganic dental filler of claim 1, wherein A is —O—C(O)—CH=$CH_2$ or —O—C(O)—C($CH_3$)=$CH_2$.

8. The surface-treated inorganic dental filler of claim 1, wherein $R^{Si}$ is —Si(OCH$_3$)$_3$ or —Si(OCH$_2$CH$_3$)$_3$.

9. The surface-treated inorganic dental filler of claim 1, wherein the inorganic filler is a non acid-reactive filler.

10. The surface-treated inorganic dental filler of claim 1, wherein the inorganic filler comprises nano-particles, clusters of nano-particles, metal oxide particles, silica particles, zirconia particles, aluminosilicate glasses, doped aluminosilicate glasses, and a combination thereof.

11. The surface-treated inorganic dental filler of claim 1, wherein the particles have at least 25% of the surface modified with the at least one silane.

12. A hardenable dental composition comprising:
a surface-treated inorganic filler of claim 1; and
at least one polymerizable resin.

13. The hardenable dental composition of claim 12, further comprising an initiator system selected from the group consisting of photoinitiator systems, redox initiator systems, peroxide heat activated, and a combination thereof.

14. A method of preparing a surface-treated inorganic dental filler according to claim 1, the method comprising contacting an inorganic filler with at least one silane of Formula I.

15. A method of preparing a surface-treated inorganic dental filler according to claim 3, the method comprising contacting an inorganic filler with at least one silane of Formula II.

16. A hardened dental composition comprising a surface-treated inorganic filler according to claim 1.

17. A method of preparing a hardenable dental composition, the method comprising:
contacting a surface-treated inorganic dental filler of claim 1 with a polymerizable resin under conditions effective to form the hardenable dental composition.

18. The surface-treated inorganic dental filler of claim 1, at least one silane selected from:

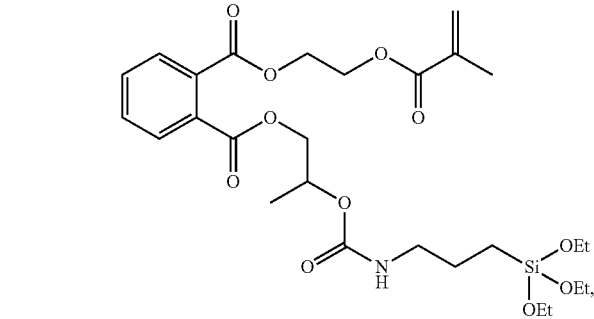

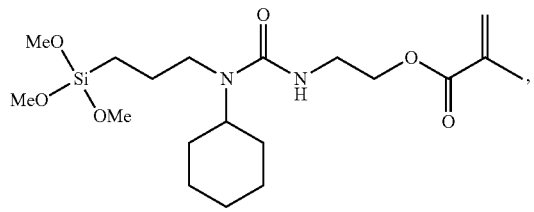

-continued
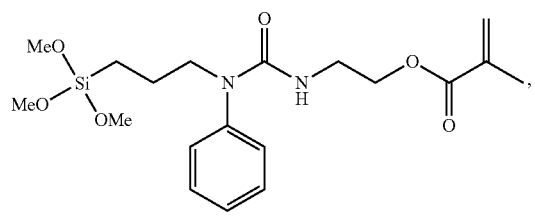
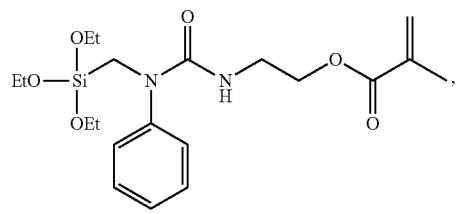
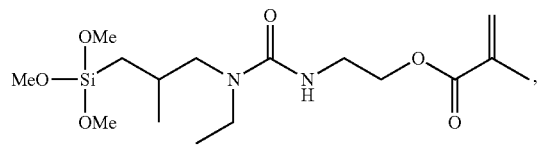
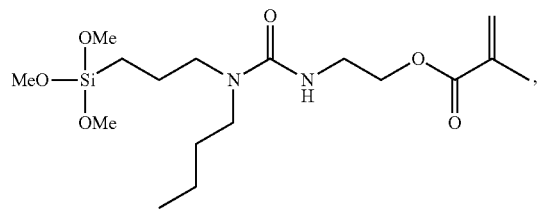
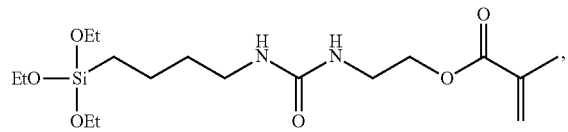
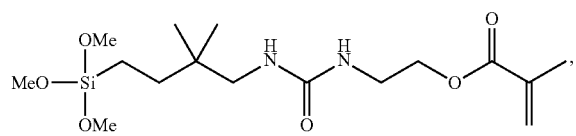
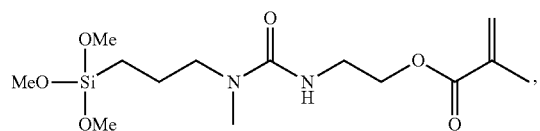
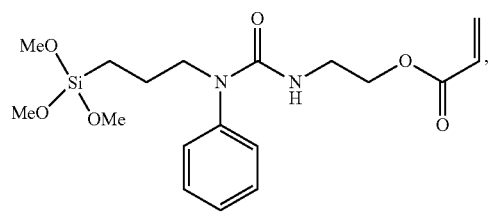
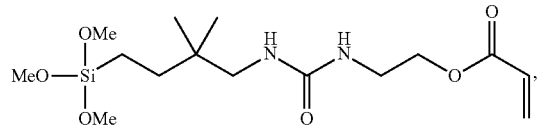
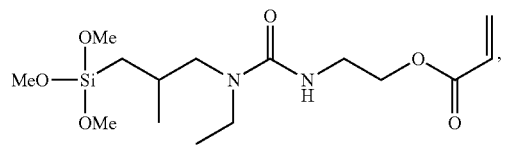

-continued
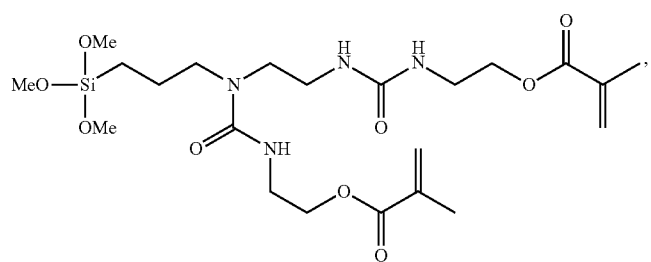
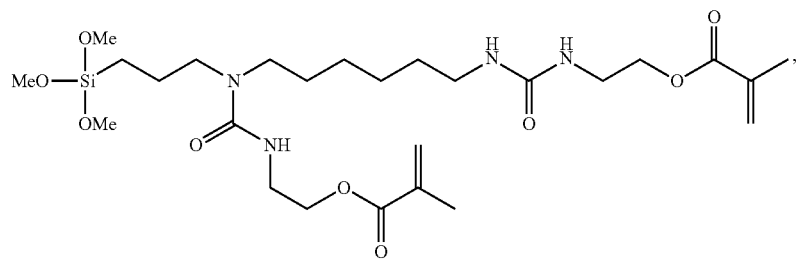
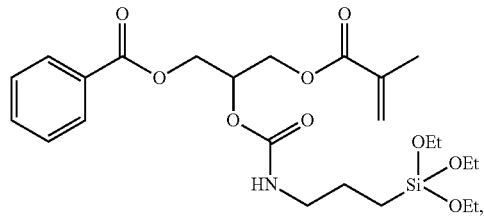
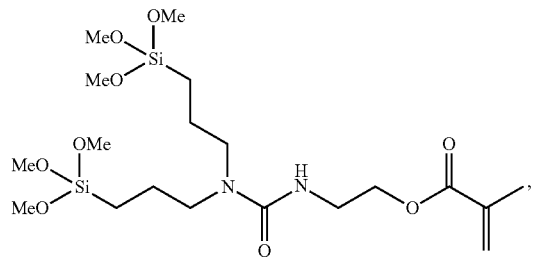
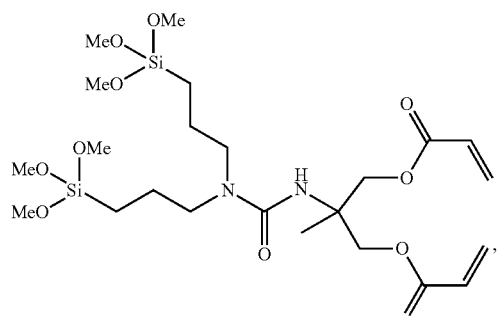
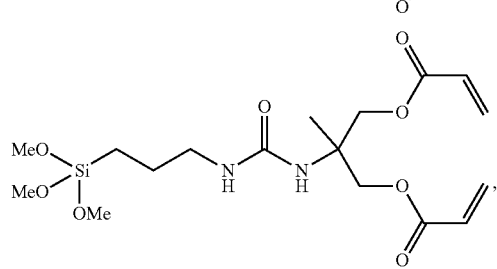

-continued
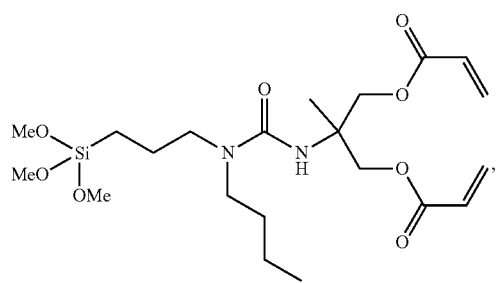
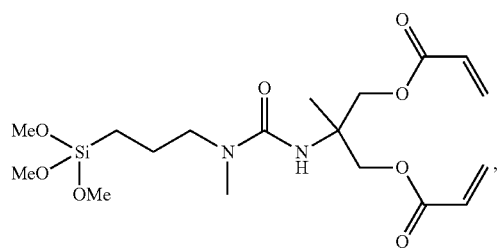
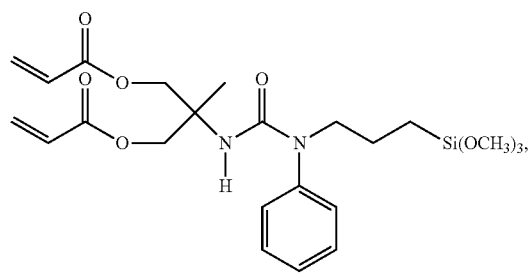
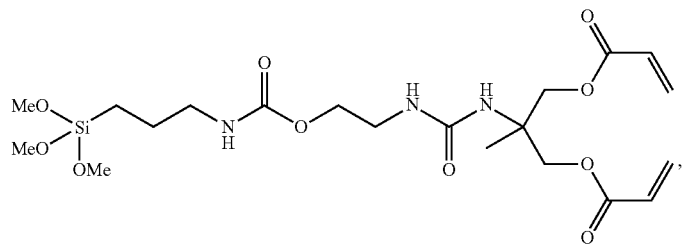
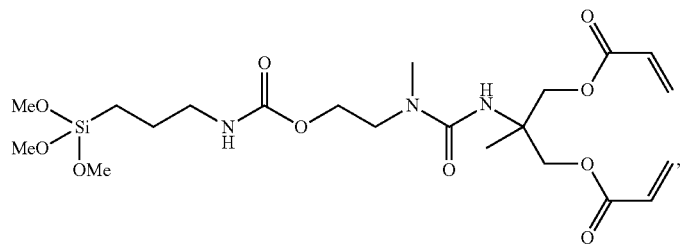

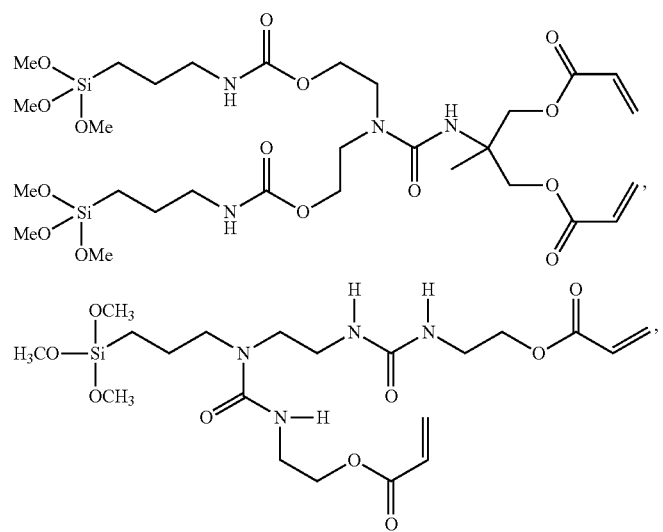
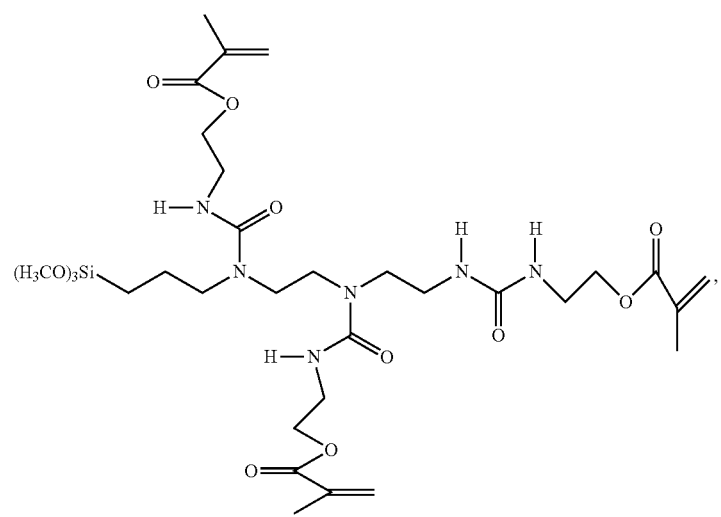
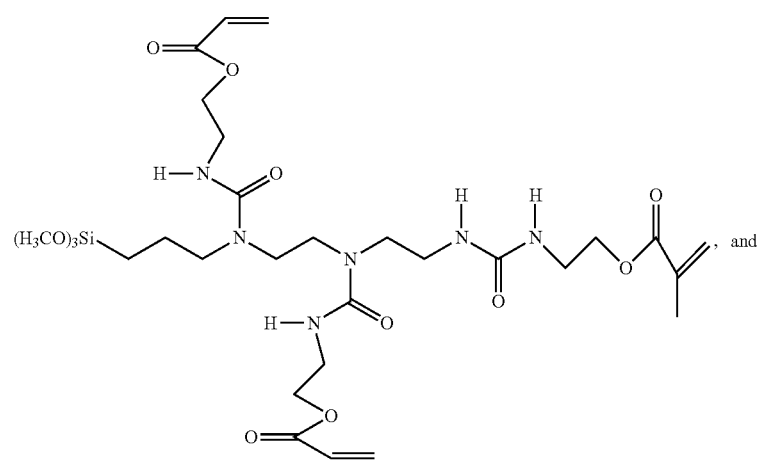

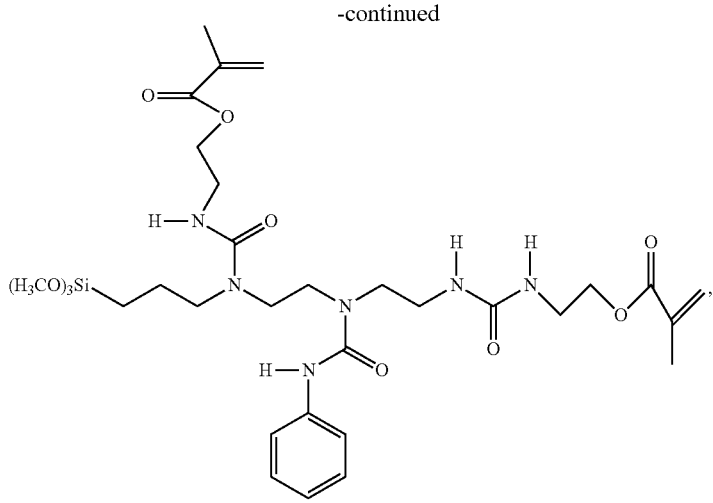

wherein Me is —CH$_3$, and Et is —CH$_2$CH$_3$.

19. A hardenable dental composition comprising:
a surface-treated inorganic dental filler of claim 18; and at least one polymerizable resin.

20. A surface-treated inorganic dental filler comprising:
an inorganic filler comprising particles having a surface modified with at least one silane represented by Formula I:

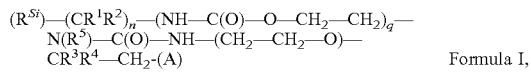

Formula I, wherein:
- each R$^{Si}$ is independently a silane-containing group of the formula —Si(Y$_p$)(R$^6$)$_{3-p}$;
- Y is a hydrolysable group;
- each R$^1$, R$^2$, and R$^3$ is independently selected from H, an alkyl group, an aryl group, an alkaryl group, and an aralkyl group;
- each R$^4$ is independently selected from H, an alkyl group, an aryl group, an alkaryl group, an aralkyl group, and a group of the formula —(CH$_2$)$_m$-(A);
- each A is independently a (meth)acryl group of the formula X$^t$—C(O)—C(R$^7$)=CH$_2$;
- X$^t$ is —O—, —S—, or —NR$^7$
- R$^5$ is H, an alkyl group, a cycloalkyl group, an aryl group, an alkaryl group, an aralkyl group, a group of the formula (R$^{Si}$)—(CR$^1$R$^2$)$_n$—(NH—C(O)—O—CH$_2$—CH$_2$)$_q$—, a group of the formula (R$^{Si}$)—(CR$^1$R$^2$)$_n$—NH—C(O)—N(R')—(CH$_2$)$_m$—, a group of the formula —(CH$_2$)$_m$-(A), a group of the formula —(CH$_2$)$_m$—N(R')—C(O)—NH—(CH$_2$—CH$_2$—O)$_t$—CR$^3$R$^4$—CH$_2$-(A), or a group of the formula —(CH$_2$)$_m$—N(R')—C(O)—NH—R$^9$;
- R$^6$ is a monovalent alkyl or aryl group;
- each R$^7$ is independently H or a C$_1$-C$_4$ alkyl group;
- R$^8$ is H or a group of the formula —(CH$_2$)$_m$—NH—C(O)—NH—(CH$_2$—CH$_2$—O)$_t$—CR$^3$R$^4$—CH$_2$-(A), a group of the formula —(CH$_2$)$_m$—NH—C(O)—NH—(CR$^1$R$^2$)—(R$^{Si}$), or a group of the formula —(CH$_2$)$_m$—NH—C(O)—NH—R$^9$,
- each R$^9$ is independently selected from an alkyl group, an aryl group, an alkaryl group, and an aralkyl group;
- each m is independently an integer selected from 1 to 6;
- each n is independently an integer selected from 1 to 6;
- p is an integer selected from 1, 2, and 3
- each q is independently 0 or 1; and
- each t is independently 0 or 1, with the proviso that at least one of R$^1$, R$^2$, R$^3$, R$^4$, and R$^5$, as shown in Formula I, is not H, and
with the proviso that the silane is not of the following formula:

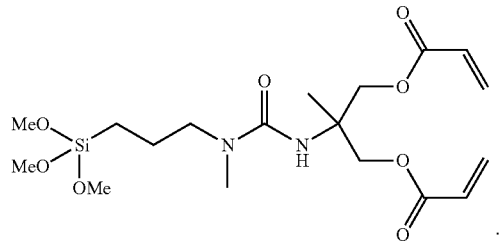

* * * * *

UNITED STATES PATENT AND TRADEMARK OFFICE
CERTIFICATE OF CORRECTION

PATENT NO. : 11,103,425 B2
APPLICATION NO. : 16/954742
DATED : August 31, 2021
INVENTOR(S) : Bradley Dene Craig Page 1 of 2

It is certified that error appears in the above-identified patent and that said Letters Patent is hereby corrected as shown below:

In the Claims

Column 53
Line 43-45 (approx.), In Claim 1, delete

"$(R^{Si})-(CR^1R^2)_n-(NH-C(O)-O-CH_2-CH_2)_q-N(R^5)-C(O)-NH-(CH_2-CH_2-O)-CR^3R^4-CH_2-(A)$" and insert -- $(R^{Si})-(CR^1R^2)_n-(NH-C(O)-O-CH_2-CH_2)_q-N(R^5)-C(O)-NH-(CH_2-CH_2-O)_r-CR^3R^4-CH^2-(A)$ --, therefor.

Line 58, In Claim 1, delete "$X^1$"" and insert -- $X^1$ --, therefor.

Line 62-63, In Claim 1, delete "$(R^{Si})-(CR^1R^2)_n-NH-C(O)-N(R^1)-(CH_2)_m-$" and insert -- $(R^{Si})-(CR^1R^2)_n-NH-C(O)-N(R^8)-(CH_2)_m-$ --, therefor.

Line 64-66, In Claim 1, delete "$-(CH_2)_m-N(R')-C(0)-NH-(CH_2-CH_2-O)_r-CR^3R^4-CH2-(A)$" and insert -- $-(CH_2)_m-N(R^8)-C(O)-NH-(CH_2-CH_2-O)_r-CR^3R^4-CH2-(A)$ --, therefor.

Column 56
Line 16, In Claim 12, before "filler", insert -- dental --.

Line 31 (approx.), In Claim 16, before "filler", insert -- dental --.

Signed and Sealed this
Seventh Day of February, 2023

Katherine Kelly Vidal
*Director of the United States Patent and Trademark Office*

CERTIFICATE OF CORRECTION (continued)
U.S. Pat. No. 11,103,425 B2

Column 63

In Claim 18, delete " 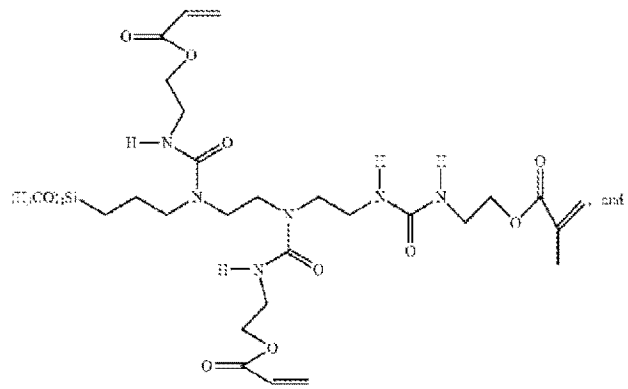 "

and insert -- 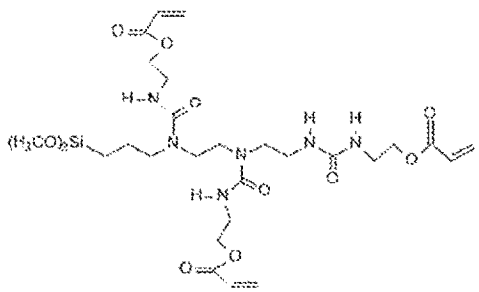 --, therefor.

Column 65
Line 30-32 (approx.), In Claim 20, delete
" $(R^{Si})-(CR^1R^2)_n-(NH-C(O)-O-CH_2-CH_2)_q-N(R^5)-C(O)-NH-(CH_2-CH_2-O)_t-CR^3R^4-CH_2-(A)$ " and insert -- $(R^{Si})-(CR^1R^2)_n-(NH-C(O)-O-CH_2-CH_2)_q-N(R^5)-C(O)-NH-(CH_2-CH_2-O)_t-CR^3R^4-CH^2-(A)$ --, therefor.

Line 45, In Claim 20, delete "X¹" and insert -- $X^1$ --, therefor.

Line 51-53, In Claim 20, delete "$-(CH_2)_m-N(R^1)-C(O)-NH-(CH_2-CH_2-O)_t-CR^3R^4-CH_2-(A)$" and insert -- $-(CH_2)_m-N(R^8)-C(O)-NH-(CH_2-CH_2-O)_t-CR^3R^4-CH_2-(A)$ --, therefor.

Line 54, In Claim 20, delete "$-(CH_2)_m-N(R^1)-C(O)-NH-R^9$" and insert -- $-(CH_2)_m-N(R^8)-C(O)-NH-R^9$ --, therefor.

Column 66
Line 26-27 (approx.), In Claim 20, delete "$-(CH_2)_m-NH-C(O)-NH-(CR^1R^2)-(R^{Si})$" and insert -- $-(CH_2)_m-NH-C(O)-NH-(CR^1R^2)_n-(R^{Si})$ --, therefor.